US010522432B2

(12) United States Patent
Gietler et al.

(10) Patent No.: US 10,522,432 B2
(45) Date of Patent: Dec. 31, 2019

(54) SEMICONDUCTOR CHIP

(71) Applicant: Infineon Technologies AG, Neubiberg (DE)

(72) Inventors: Herbert Gietler, Villach (AT); Robert Pressl, Klagenfurt (AT)

(73) Assignee: Infineon Technologies AG, Neubiberg (DE)

( * ) Notice: Subject to any disclaimer, the term of this patent is extended or adjusted under 35 U.S.C. 154(b) by 0 days.

(21) Appl. No.: 15/413,442

(22) Filed: Jan. 24, 2017

(65) Prior Publication Data
US 2017/0133289 A1    May 11, 2017

Related U.S. Application Data

(63) Continuation of application No. 14/555,735, filed on Nov. 28, 2014, now Pat. No. 9,589,914.

(51) Int. Cl.
*H01L 23/58* (2006.01)
*H01L 21/66* (2006.01)
(Continued)

(52) U.S. Cl.
CPC ............. *H01L 22/34* (2013.01); *G01N 27/24* (2013.01); *G01R 31/2601* (2013.01); *G01R 31/2831* (2013.01); *G01R 31/2856* (2013.01); *H01L 21/78* (2013.01); *H01L 23/58* (2013.01); *H01L 23/585* (2013.01); *H01L 23/642* (2013.01); *H01L 29/0649* (2013.01); *H01L 29/0684* (2013.01); *H01L 2224/291* (2013.01); *H01L 2224/2919* (2013.01); *H01L 2224/32225* (2013.01); *H01L 2224/32245* (2013.01); *H01L 2224/48227* (2013.01); *H01L 2224/48247* (2013.01); *H01L 2924/0002* (2013.01)

(58) Field of Classification Search
CPC . H01L 23/58; H01L 23/5222; H01L 29/0649; H01L 29/0684; G01R 31/2601
See application file for complete search history.

(56) References Cited

U.S. PATENT DOCUMENTS

| 2004/0129938 A1 | 7/2004 | Landers et al. |
| 2007/0262370 A1 | 11/2007 | Okada |

(Continued)

FOREIGN PATENT DOCUMENTS

| CN | 101217158 A | 7/2008 |
| CN | 101236920 A | 8/2008 |

(Continued)

OTHER PUBLICATIONS

German Office Action issued for corresponding application No. 10 2015 120 541.6, dated Jun. 5, 2019, 6 pages.
(Continued)

*Primary Examiner* — Fernando L Toledo
*Assistant Examiner* — Neil R Prasad
(74) *Attorney, Agent, or Firm* — Viering, Jentschura & Partner MBB

(57) ABSTRACT

According to various embodiments, a semiconductor chip may include: a semiconductor body region including a first surface and a second surface opposite the first surface; a capacitive structure for detecting crack propagation into the semiconductor body region; wherein the capacitive structure may include a first electrode region at least partially surrounding the semiconductor body region and at least substantially extending from the first surface to the second surface; wherein the capacitive structure further may include a second electrode region disposed next to the first electrode region and an electrically insulating region extending between the first electrode region and the second electrode region.

18 Claims, 16 Drawing Sheets

(51) Int. Cl.
*H01L 29/06* (2006.01)
*G01R 31/26* (2014.01)
*G01N 27/24* (2006.01)
*G01R 31/28* (2006.01)
*H01L 23/64* (2006.01)
*H01L 21/78* (2006.01)

(56) References Cited

U.S. PATENT DOCUMENTS

| | | | |
|---|---|---|---|
| 2008/0041615 A1* | 2/2008 | Zhong | H05K 3/285 174/255 |
| 2008/0179710 A1 | 7/2008 | Yip et al. | |
| 2008/0246491 A1* | 10/2008 | Ogawa | G01R 31/2853 324/519 |
| 2010/0051337 A1* | 3/2010 | Nakamura | H05K 1/141 174/258 |
| 2012/0092033 A1 | 4/2012 | Shao et al. | |
| 2013/0187280 A1* | 7/2013 | Yuan | H01L 23/481 257/773 |
| 2014/0346509 A1* | 11/2014 | Zundel | H01L 29/7397 257/48 |

FOREIGN PATENT DOCUMENTS

| | | |
|---|---|---|
| CN | 102445649 A | 5/2012 |
| CN | 103308095 A | 9/2013 |

OTHER PUBLICATIONS

Chinese Office Action issued for corresponding application No. 201510846568.X, dated May 31, 2019, 10 pages.

\* cited by examiner

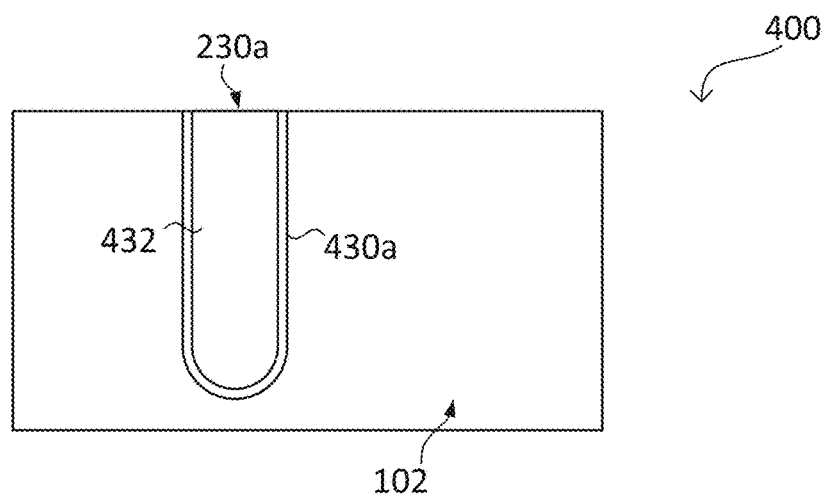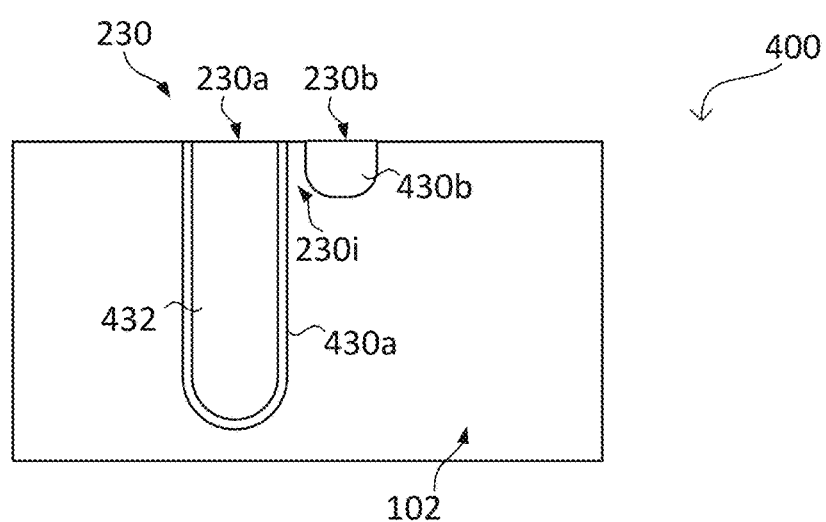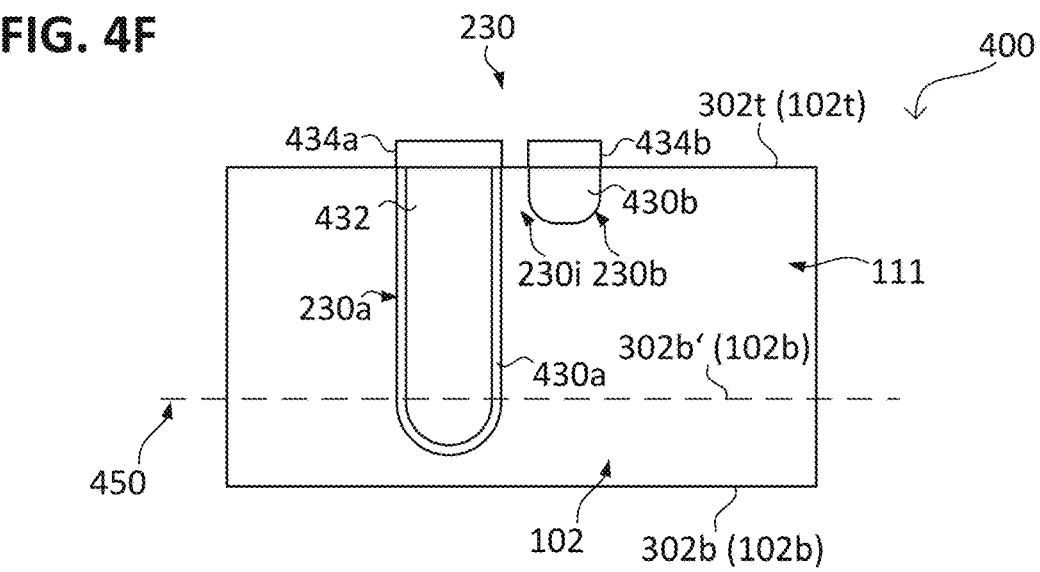

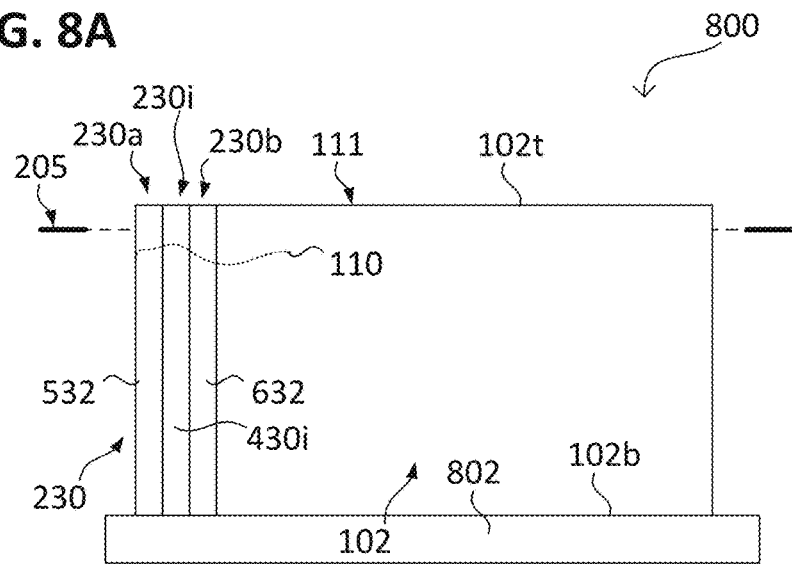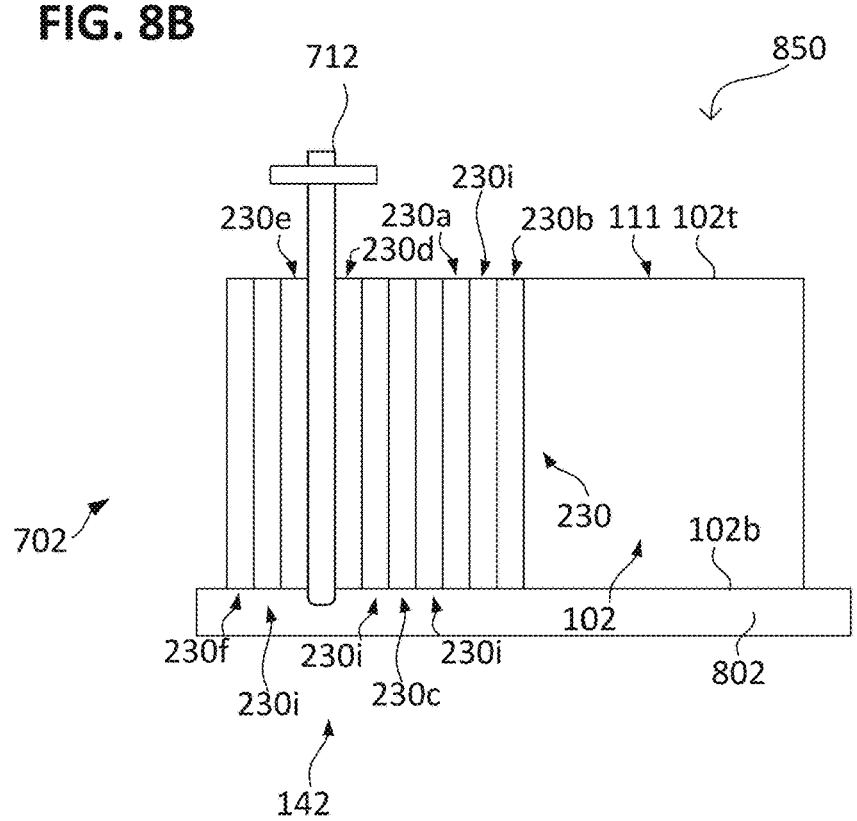

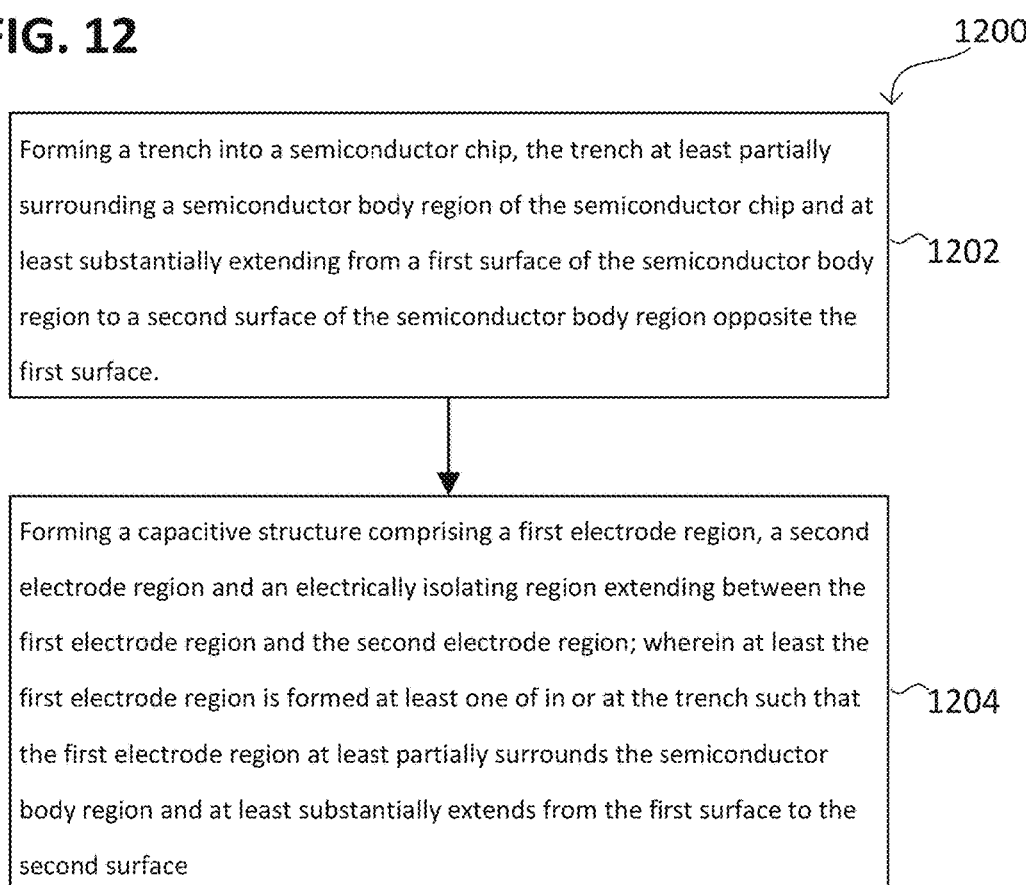

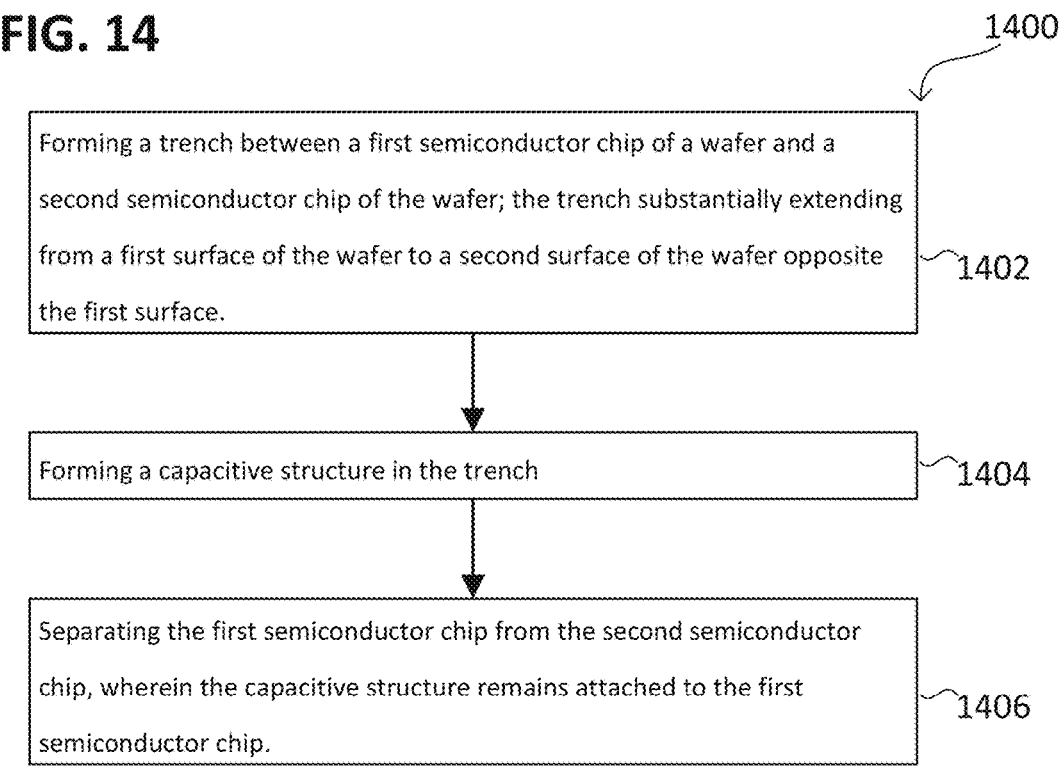

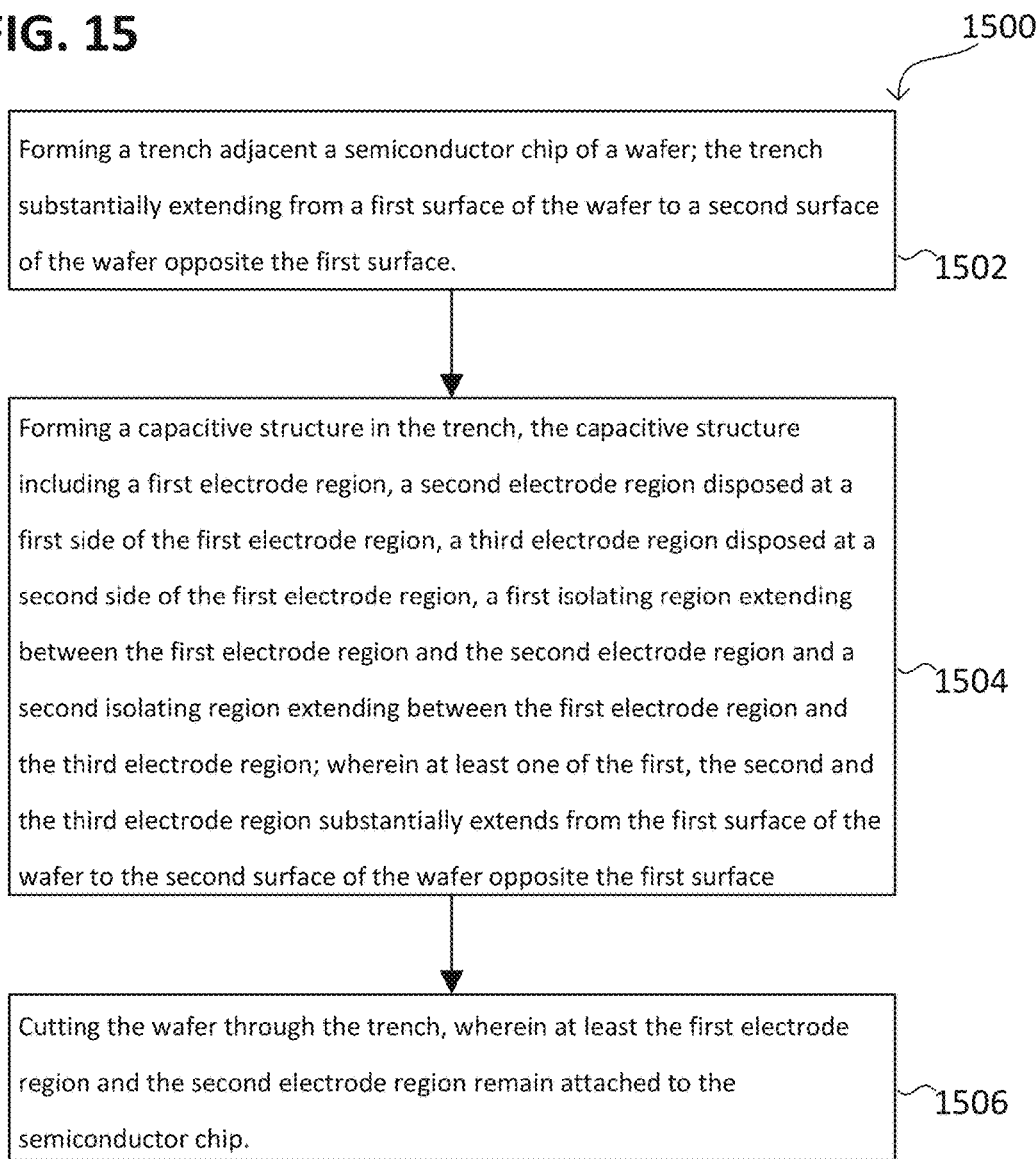

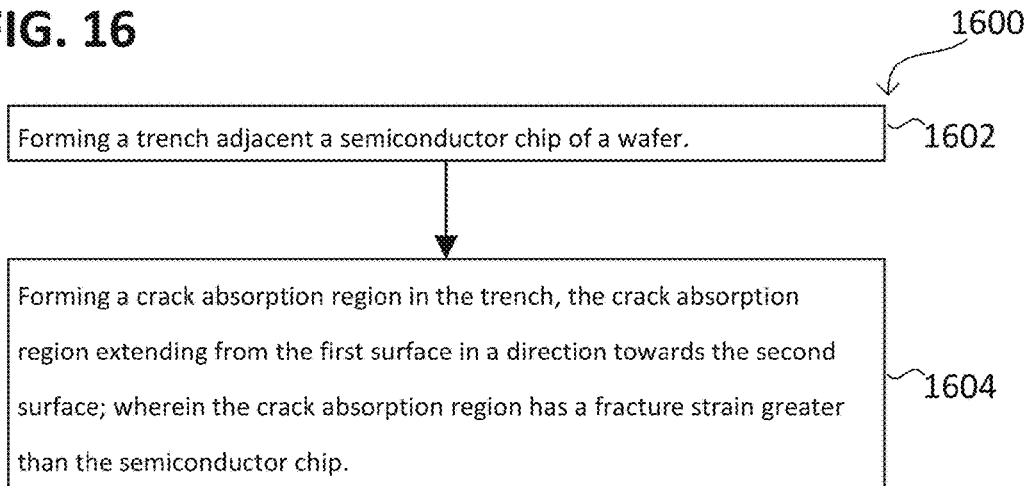
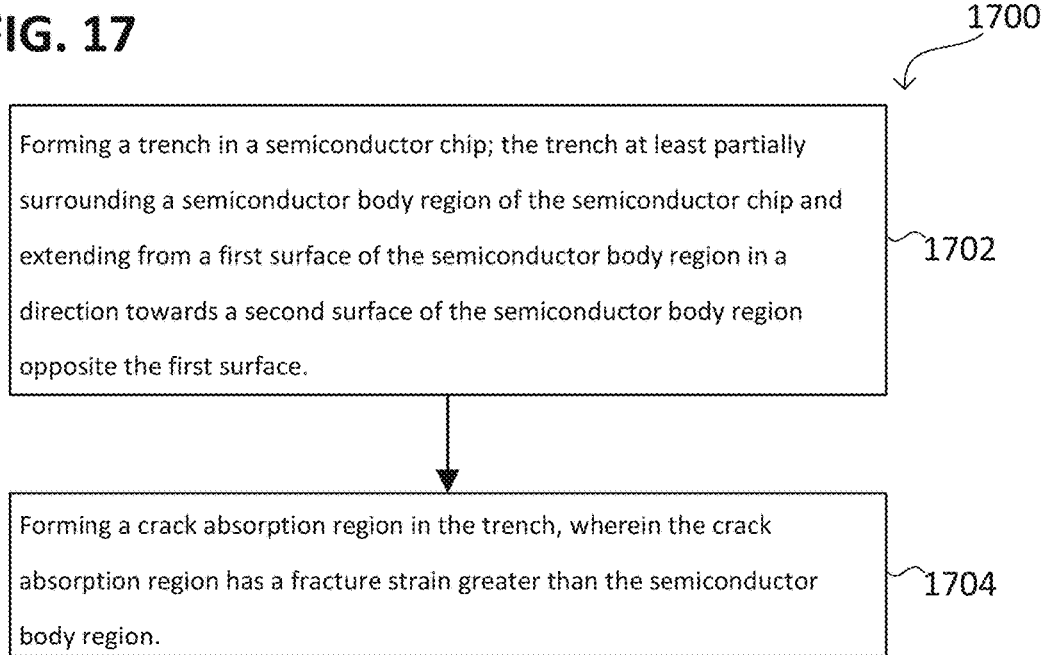

SEMICONDUCTOR CHIP

RELATED APPLICATION(S)

This application is a continuation of U.S. patent application Ser. No. 14/555,735, entitled "SEMICONDUCTOR CHIP", which was filed Nov. 28, 2014, and is incorporated herein by reference in its entirety.

TECHNICAL FIELD

Various embodiments relate generally to a semiconductor chip.

BACKGROUND

In general, a semiconductor chip (also called integrated circuit, IC, chip, or microchip) may be processed in semiconductor technology on and/or in a wafer (or a substrate or a carrier). The wafer may include a plurality of semiconductor chips in corresponding regions of the wafer. During processing, the semiconductor chip may be damaged by mechanical stress. For example, mechanical stress may occur e.g. during singulating the semiconductor chip from the wafer, during handling the semiconductor chip by positioning systems (also called Pick-and-Place applications) or during thermally treating the semiconductor chip, e.g. during encapsulation or soldering the semiconductor chip.

Such mechanical stress may cause crack formation and crack propagation in the semiconductor chip. The impact of a crack on a semiconductor chip (or a device operating the semiconductor chip) may result in an uncontrolled or undefined behavior, e.g. failure or malfunction, of the semiconductor chip. Conventional methods or sensors for the detection of chip cracks in a semiconductor chip may be limited in their reliability, resulting in undetected cracks, wherein increasing their reliability may be time-consuming and cost intensive.

SUMMARY

According to various embodiments, a semiconductor chip may include: a semiconductor body region including a first surface and a second surface opposite the first surface; a capacitive structure for detecting crack propagation into the semiconductor body region; wherein the capacitive structure may include a first electrode region at least partially surrounding the semiconductor body region and at least substantially extending from the first surface to the second surface; wherein the capacitive structure further may include a second electrode region disposed next to the first electrode region and an electrically insulating region extending between the first electrode region and the second electrode region.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which:

FIG. 3A and FIG. 3B respectively show a semiconductor chip according to various embodiments;

FIG. 4A to FIG. 4F respectively show a semiconductor chip at various stages during processing according to various embodiments;

FIG. 8A and FIG. 8B respectively show a semiconductor chip at various stages during processing according to various embodiments;

FIG. 12 shows a schematic flow diagram of a method of processing a semiconductor chip according to various embodiments;

FIG. 14 shows a schematic flow diagram of a method of processing a wafer according to various embodiments;

FIG. 15 shows a schematic flow diagram of a method of processing a wafer according to various embodiments;

FIG. 16 shows a schematic flow diagram of a method of processing a wafer according to various embodiments; and FIG. 17 shows a schematic flow diagram of a method of processing a semiconductor chip according to various embodiments.

DESCRIPTION

Figure 1A:
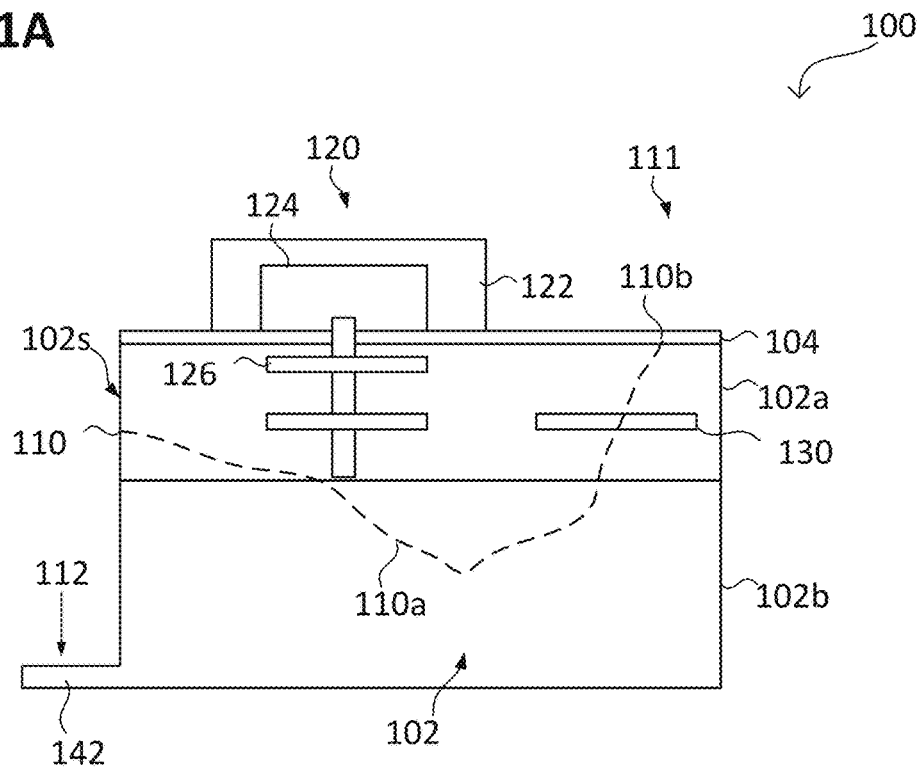
FIG. 1A and FIG. 1B respectively show a semiconductor chip including a conventional crack sensor.

The following detailed description refers to the accompanying drawings that show, by way of illustration, specific details and embodiments in which the invention may be practiced.

The word "exemplary" is used herein to mean "serving as an example, instance, or illustration". Any embodiment or design described herein as "exemplary" is not necessarily to be construed as preferred or advantageous over other embodiments or designs.

The word "over" used with regards to a deposited material formed "over" a side or surface may be used herein to mean that the deposited material may be formed "directly on", e.g. in direct contact with, the implied side or surface. The word "over" used with regards to a deposited material formed "over" a side or surface, may be used herein to mean that the deposited material may be formed "indirectly on" the implied side or surface with one or more additional layers being arranged between the implied side or surface and the deposited material.

The term "lateral" used with regards to the "lateral" extension of a structure (or of a substrate, a wafer, or a carrier) or "laterally" next to, may be used herein to mean an extension or a positional relationship along a surface of a substrate, a wafer, or a carrier. That means that a surface of a substrate (e.g. a surface of a carrier, or a surface of a wafer) may serve as reference, commonly referred to as the main processing surface of the substrate (or the main processing surface of the carrier or wafer). Further, the term "width" used with regards to a "width" of a structure (or of a structure element) may be used herein to mean the lateral extension of a structure. Further, the term "height" used with regards to a height of a structure (or of a structure element), may be used herein to mean an extension of a structure along a direction perpendicular to the surface of a substrate (e.g. perpendicular to the main processing surface of a substrate). The term "thickness" used with regards to a "thickness" of a layer may be used herein to mean the spatial extension of the layer perpendicular to the surface of the support (the material) on which the layer is deposited. If the surface of the support is parallel to the surface of the substrate (e.g. to the main processing surface) the "thickness" of the layer deposited on the support may be the same as the height of the layer. Further, a "vertical" structure may be referred to as a structure extending in a direction perpendicular to the lateral direction (e.g. perpendicular to the main processing surface of a substrate) and a "vertical" extension may be referred to as an extension along a direction perpendicular to the lateral direction (e.g. an extension perpendicular to the main processing surface of a substrate).

The term "forming" with regards to a layer, a material or a region may refer to disposing, arranging or depositing the layer, the material or the region. A method for forming, e.g. a layer, a material, a region, etc., may include various deposition methods which among others may be: chemical vapor deposition, physical vapor deposition (e.g. for dielectric materials), electrodeposition (also called electroplating, e.g. for metals or metal alloys) or spin coating (e.g. for fluid materials). Generally, a vapor deposition may be performed by sputtering, laser ablation, cathodic arc vaporization or thermal evaporation. A method for forming metals may include metal plating, e.g. electroplating or chemical plating.

The term "forming" with regards to a layer, a material or a region may also include a chemical reaction or fabricating a chemical composition, where e.g. at least a portion of the layer, the material or the region is formed by a transformation of one set of chemical substances into the chemical composition. "Forming" may for example include changing the positions of electrons by breaking or forming chemical bonds between atoms of the set of chemical substances. "Forming" may further include oxidation and reduction, complexation, precipitation, an acid-base reaction, a solid-state reaction, substitution or doping, addition and elimination, diffusion or a photochemical reaction. "Forming" may, for example, change the chemical and physical properties of the set of chemical substances which chemically compose the portion of the layer, the material or the region which may be among others electrical conductivity, phase composition, optical properties, etc. "Forming" may for example include the application of a chemical reagent to a mother compound to change the chemical and physical properties of the mother compound.

According to various embodiments, a semiconductor chip may be singulated from a wafer by removing material from a kerf region of the wafer (also called dicing or cutting the wafer). For example, removing material from the kerf region of the wafer may be processed by scribing and breaking, cleavage, blade dicing or mechanical sawing (e.g. using a dicing saw). In other words, the semiconductor chip may be singulated by a wafer dicing process. After the wafer dicing process the semiconductor chip may be electrically contacted and encapsulated, e.g. by mold materials, into a chip carrier (also called a chip housing) which may then be suitable for use in electronic devices such as computers. For example, the semiconductor chip may be bonded to a chip carrier by wires, and the chip carrier may be soldered onto a printed circuit board.

According to various embodiments, a semiconductor chip may include a semiconductor body made of semiconductor materials of various types, including a group IV semiconductor (e.g. silicon or germanium), a compound semiconductor, e.g. a group III-V compound semiconductor (e.g. gallium arsenide) or other types, including group III semiconductors, group V semiconductors or polymers, for example. In an embodiment, the semiconductor body is made of silicon (doped or undoped), in an alternative embodiment, the semiconductor body is a silicon on insulator (SOI) wafer. As an alternative, any other suitable semiconductor material can be used for the semiconductor body, for example semiconductor compound material such as gallium phosphide (GaP), indium phosphide (InP), but also any suitable ternary semiconductor compound material or quaternary semiconductor compound material such as indium gallium arsenide (InGaAs).

According to various embodiments, a semiconductor chip may further include a passivation layer for protecting the semiconductor body of the semiconductor chip from environmental influences, e.g. oxidation. The passivation layer may include a metal oxide, an oxide of the semiconductor body, e.g. silicon oxide, a nitride, e.g. silicon nitride, a polymer, e.g. benzocyclobutene (BCB) or polyimide (PI), a resin, a resist, or a dielectric material.

According to various embodiments, a semiconductor chip may include a seal ring for electrically grounding the semiconductor body of the semiconductor chip. The seal ring may include an electric lead (power metal) running on the semiconductor body and electrically connected to a conduction structure in the semiconductor body. The conduction structure may include a metal or metal alloy extending into the semiconductor body. Further, the seal ring may include a protection structure, e.g. a cover layer including imide.

According to various embodiments, a metal may include one element of the following group of elements: aluminum, copper, nickel, magnesium, chromium, iron, zinc, tin, gold, silver, iridium, platinum or titanium. According to various embodiments, a metal alloy may include one element or more than one element of the group of elements. For example a metal alloy may include an intermetallic compound, e.g. an intermetallic compound of gold and aluminum, an intermetallic compound of copper and aluminum, an intermetallic compound of copper and zinc ("brass") or an intermetallic compound of copper and tin ("bronze").

According to various embodiments, a semiconductor chip may include an active chip area. The active chip area may be disposed in a portion of the semiconductor body (in other words, a semiconductor body region) and may include one or more transistors, resistors and capacitors which may be configured to perform computing or storage operations. The active chip area may be a few micrometers thick, and may extend along a top side of the semiconductor body. In other words, the active chip area may be part of a semiconductor body region or may refer to a semiconductor body region. Under the active chip area, a bottom portion of the semiconductor body region may extend. The bottom portion of the semiconductor body (also called base layer) may be thicker than the active chip area, e.g. a few hundreds of micrometers thick, and may extend along a bottom side of the semiconductor body.

FIG. 1A illustrates a semiconductor chip 100 including a conventional crack sensor 130 in a cross-sectional view during processing the semiconductor chip 100, e.g. during singulation 112 of the semiconductor chip 100 from a wafer (e.g. compare FIG. 7A) by removing 112 material from a kerf region 142 of the wafer, in other words, during wafer dicing 112.

The semiconductor chip 100 may include a semiconductor body 102 with a semiconductor body region 111. For example, the semiconductor body region 111 may include an active area of the semiconductor chip 100. Further, the semiconductor chip 100 may include a passivation layer 104 and a seal ring 120 with a protection structure 122 over a power metal 124, the power metal 124 electrically connected to a conduction structure 126.

During processing the semiconductor chip 100 (or a device operating the semiconductor chip 100), a chip crack 110 (also referred as crack 110) may occur, e.g. the chip crack 110 may appear at a sidewall 102s of the semiconductor chip 100 or a sidewall 102s of the semiconductor body region 111 and may propagate from the sidewall 102s to the interior of the chip 100. Such a chip crack 100 may occur due to a variety of reasons and during a variety of methods of processing the semiconductor chip 100, e.g. during wafer dicing or handling the semiconductor chip 100 (e.g. by a Pick-and-Place application) or soldering the semiconductor chip 100 (or a device operating the semiconductor chip 100), as described herein.

The length of a chip crack 110 directly after processing the semiconductor chip 100 may be short and thus, the chip crack 110 may not yet have propagated into the semiconductor body region 111 (active area) or any circuit components in the semiconductor body region 111. However, the length of a chip crack 110 may grow during further processing the semiconductor chip 100 or during operating the semiconductor chip 100 itself, e.g. after encapsulating the semiconductor chip 100 and using the semiconductor chip 100 in a device. As illustrated in FIG. 1A a chip crack 110 may propagate 110a into the semiconductor body 102 of a semiconductor chip 100, further continue propagating 110b into the active chip area 111 and may surface in the active chip area 111. Conventional screening methods to detect chip cracks 110, e.g. before they impair the semiconductor chip 100 behavior or the semiconductor chip 100 functionality may be time consuming, complicated or unreliable.

A conventional screening method for electrical detection of chip crack 110 propagation may include a stress test, e.g. stressing the semiconductor chip 100 at elevated temperatures, a so called Burn-in stress test, or applying several temperature cycles to the semiconductor chip 100 by reflow soldering simulation. Applying the stress test to a semiconductor chip 100 with a chip crack 110 may induce the propagation of the chip crack 110 until the chip crack 110 enters a crack detection area, e.g. the active area 111 of the semiconductor chip 100, where the chip crack 110 can be detected and filtered by electrical testing methods (e.g. by detecting malfunction of circuit components in the active area 111).

Applying a stress test may potentially be insufficient, e.g. a testing duration may be too short, to induce chip crack propagation 110 continuing into the crack detection area provided by the active area 111. Thus, although stress tests were applied to a semiconductor chip 100, a chip crack 110 may remain undetected. The semiconductor chip 100 may fail due to the undetected chip crack 110 since the undetected chip crack 110 may propagate into the active chip area 111 after operating the semiconductor chip 100 for a certain time. The semiconductor chip 100 may fail, thereby causing an undefined behavior of the semiconductor chip 100.

Beside chip cracks 110 which are present in the semiconductor chip 100 during processing the semiconductor chip 100 (e.g. if a stress test was insufficient to detect the chip crack 110), chip cracks 110 may also occur during operation of the semiconductor chip 100 (or a device operating the semiconductor chip 100), e.g. during continuous operation or after operating the semiconductor chip 100 for a time period longer than conventional stress tests may be able to simulate.

A conventional crack sensor 130 (also called a perimeter line 130) for the detection of chip cracks 110 may include a metal wire which runs along the surface of the semiconductor chip 100 (e.g. the surface of the silicon in the semiconductor body 102) and may surround the active chip area 111. A chip crack 110 impairing the metal wire of the perimeter line 130 may cause a change of the resistance of the perimeter line 130 and therefore the chip crack 110 may be detected based on the resistance of the perimeter line 130. In response to a chip crack 110 being detected, the semiconductor chip 100 (or a product operating the semiconductor chip 100) may be switched into a proper operating mode to avoid any undefined behavior of the semiconductor chip 100 or any critical situations. For example, the semiconductor chip 100 may be switched into a standby mode or may be shut down.

In other words, an undetected crack 110 may propagate in the semiconductor chip during operating the semiconductor chip, e.g. in an electric device, causing an undefined behavior of the semiconductor chip or the electric device. An undefined behavior of the semiconductor chip or device may lead to critical, e.g. life-threatening situations, if the undefined behavior remains undetected. For example, if the semiconductor chip is used in a car, an undefined behavior could result in airbags being triggered unintentionally.

Figure 1B:
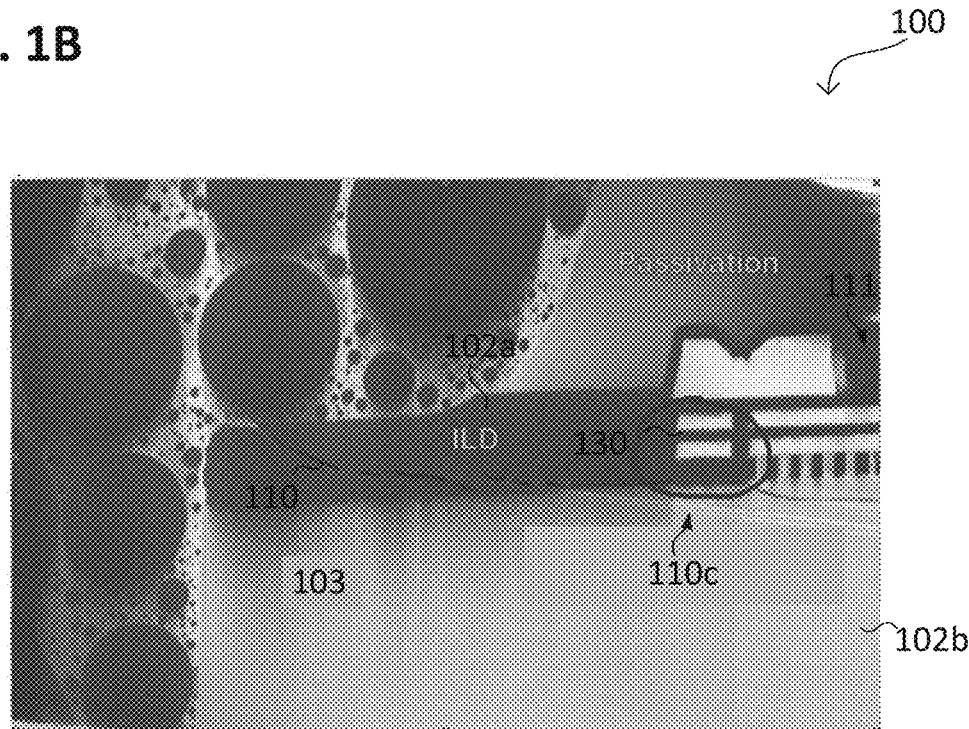

FIG. 1B illustrates a semiconductor chip 100 including a conventional crack sensor 130 in a cross-sectional view, wherein a chip crack 110 may have propagated into the semiconductor body region 111. Although using a perimeter line 130, it may be uncertain whether the chip crack 110 is detected since the perimeter line 130 extends only at the surface of the semiconductor chip 100. Therefore, the chip crack 110 potentially may pass by the perimeter line 130 (without impairing the metal wire of the perimeter line 130), as illustrated by arrow 110c in FIG. 1B. As exemplarily illustrated in FIG. 1B, the chip crack 110 may pass by underneath the perimeter line 130 and propagate into the active area 111 without being detected.

Figure 2A:
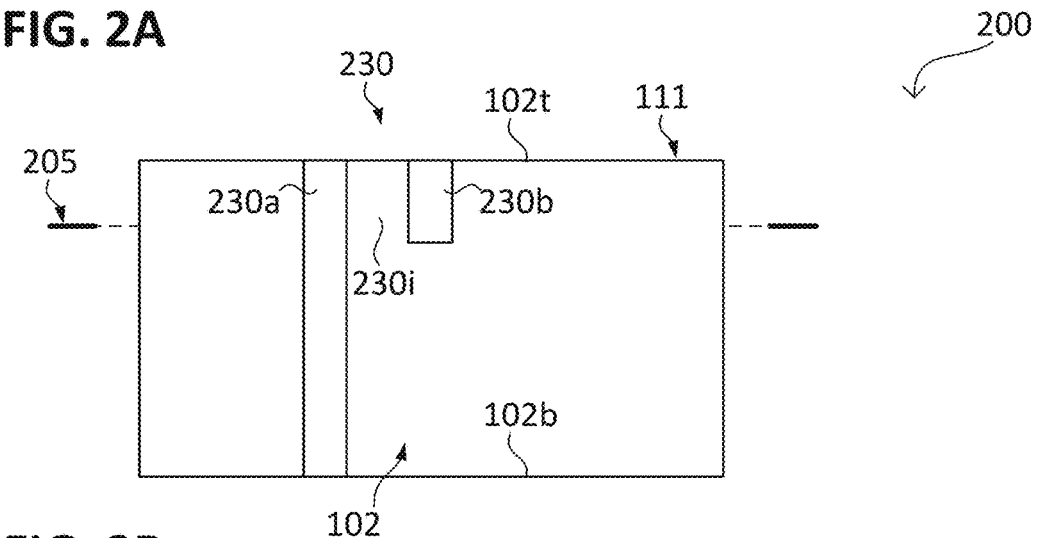
FIG. 2A to FIG. 2C respectively show a semiconductor chip according to various embodiments.
Figure 2B:
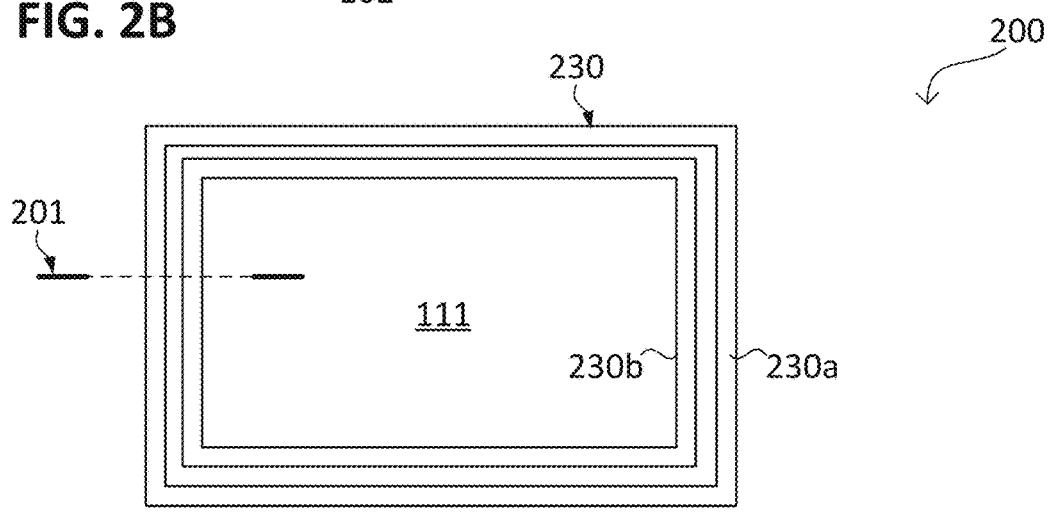
Figure 2C:
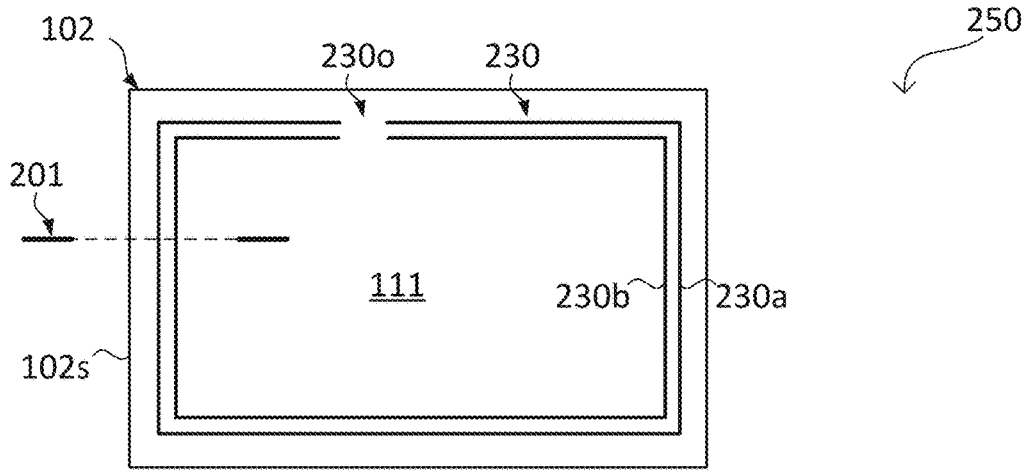

FIG. 2A illustrates a semiconductor chip 200, according to various embodiments, in a cross sectional view taken along line 201 (see FIG. 2B or FIG. 2C). The semiconductor chip 200 may include a capacitive structure 230 for detecting crack propagation into the semiconductor chip 200. The semiconductor chip 200 may include a semiconductor body 102, with a semiconductor body region 111, in other words, a portion 111 of the semiconductor body 102.

According to various embodiments, the semiconductor body region 111 may include an active area or an integrated circuit of the semiconductor chip 200. The semiconductor body region 111 may have a first surface 102t (e.g. a top side 102t of the semiconductor body region 111) and a second surface 102b (e.g. a bottom side 102b of the semiconductor body region 111) opposite the first surface 102t. In other words, the semiconductor body region 111 may extend between the first surface 102t and the second surface 102b.

According to various embodiments, the capacitive structure 230 may include a first electrode region 230a at least substantially extending from the first surface 102t to the second surface 102b. The first electrode region 230a may include an electrically conducting material, e.g. a metal, a metal alloy, a silicide (e.g. titanium silicide, molybdenum silicide, tantalum silicide or tungsten silicide), a conductive polymer, a polycrystalline semiconductor, or a doped semiconductor, e.g. tungsten, aluminum, copper, polycrystalline silicon, or doped silicon. An electrically conducting material may have an electrical conductivity (measured at room temperature and constant electric field direction) greater than about 1 S/m, e.g. greater than about $10^2$ S/m, e.g. greater than about $10^4$ S/m.

According to various embodiments, extending from the first surface 102t to the second surface 102b may be understood as to extend (vertically) through the semiconductor body 102 of the semiconductor chip 200. A region, e.g. the first electrode region 230a, at least substantially extending from the first surface 102t to the second surface 102b may refer to an extension of the region in a direction from the first surface 102t to the second surface 102b, e.g. the direction being perpendicular to the first surface 102t (in other words, a vertical extension). The extension of the region, which at least substantially extends from the first surface 102t to the second surface 102b, may be greater than about 80% of a distance between the first surface 102t and the second surface 102b in the direction from the first surface 102t to the second surface 102b, e.g. greater than about 90%, e.g. greater than about 95%. According to various embodiments, the region may completely extend from the first surface 102t to the second surface 102b. In other words, the region may extend through the entire thickness of the semiconductor body 102 or semiconductor body region 111.

According to various embodiments, the capacitive structure 230 may further include a second electrode region 230b disposed next to the first electrode region 230a. The second electrode region 230b may include an electrically conducting material, similar to the first electrode region 230a. The first electrode region 230a may be spaced at a distance from the second electrode region 230b.

According to various embodiments, the capacitive structure 230 may further include an electrically insulating region 230i extending between the first electrode region 230a and the second electrode region 230b. The electrically insulating region 230i may include an electrically insulating material, e.g. a dielectric material, e.g. a high-x dielectric or a low-x dielectric. For example, the electrically insulating material may include a resin, a resist, a semiconductor oxide, a metal oxide, a ceramic, a semiconductor nitride, a metal nitride, a semiconductor carbide, a metal carbide, a glass, e.g. fluorosilicate glass (FSG), a silicate, e.g. hafnium silicate or zirconium silicate, a silicon oxynitride, a transition metal oxide, e.g. hafnium dioxide or zirconium dioxide, an electrically insulating polymer, e.g. benzocyclobutene (BCB) or polyimide (PI), or an undoped semiconductor (e.g. undoped silicon), e.g. an undoped portion of the semiconductor body 102 between the first electrode region 230a and the second electrode region 230b, e.g. an oxidized portion of the semiconductor body 102 between the first electrode region 230a and the second electrode region 230b. An electrically insulating material may have an electrical conductivity (measured at room temperature and constant electric field direction) less than about $10^{-2}$ S/m, e.g. less than about $10^{-5}$ S/m, e.g. less than about $10^{-7}$ S/m.

According to various embodiments, the electrically insulating region 230i may be configured to electrically insulate the first electrode region 230a from the second electrode region 230b. Further, the electrically insulating region 230i may define electrical properties, e.g. a dielectric strength or a leakage current, of the capacitive structure 230. In other words, the electrically insulating region 230i may withstand an electric field between the first electrode region 230a and the second electrode region 230b up to a certain field strength without breaking down (in other words, without experiencing failure of its insulating properties, e.g. without substantially changing its electrical conductivity). The electric field between the first electrode region 230a and the second electrode region 230b may be provided by applying an electrical voltage between the first electrode region 230a and the second electrode region 230b, e.g. a bias voltage.

According to various embodiments, a chip crack 110 propagating into the first electrode region 230a or into the electrically insulating region 230i may change the electrical properties of the capacitive structure 230. For example, the dielectric strength of the capacitive structure 230 may be changed (e.g. reduced) if the electrically insulating region 230i is impaired, e.g. due to a crack 110 propagating into the electrically insulating region 230i.

FIG. 2B illustrates a semiconductor chip 200, according to various embodiments, in a plan view, or in a cross sectional view taken along line 205 (see FIG. 2A). The first electrode region 230a and the second electrode region 230b may surround the semiconductor body region 111 in a lateral direction. In other words, the capacitive structure 230 may be formed as ring structure, e.g. the capacitive structure 230 may extend along a closed path, the closed path surrounding the semiconductor body region 111.

The first electrode region 230a may surround the second electrode region 230b, as illustrated in FIG. 2B. Alternatively, according to various embodiments, the second electrode region 230b may partially surround the first electrode region 230a. Both configurations may result in a capacitive structure 230 at least partially surrounding the semiconductor body region 111 in a lateral direction.

A capacitive structure 230, according to various embodiments, may overcome potentially undetected chip cracks 110 propagating into the semiconductor body region 111 as described herein. Stress tests applied to the semiconductor chip 200 to continue chip crack 110 propagation into the crack detection area potentially may become unnecessary since the crack detection area provided by the capacitive structure 230, as illustrated in FIG. 2A and FIG. 2B, may expand into the area where chip crack 110 propagation initially occurs. A chip crack 110 propagating into the semiconductor body region 111 may need to pass at least partially through the capacitive structure 230 to enter the semiconductor body region 111. For example, chip cracks 110 passing underneath the chip detection area may be avoided since the capacitive structure 230 may substantially extend through the semiconductor body 102.

FIG. 2C illustrates a semiconductor chip 250 according to various embodiments, in a plan view or in a cross sectional view taken along line 205 (see FIG. 2A). The first electrode region 230a and the second electrode region 230b may extend along the sidewall 102s of the semiconductor body 102. A chip crack 110 emerging at the sidewall 102s of the semiconductor body 102 (e.g. after sawing into the wafer) may pass through the capacitive structure 230 since the capacitive structure 230 may be disposed adjacent to the sidewall 102s of the semiconductor body 102. Also an occurrence of chip cracks 110 passing underneath the chip detection area may be reduced since the capacitive structure 230 may substantially extend from the first surface 102t to the second surface 102b, as described herein.

According to various embodiments, the capacitive structure 230 may be formed as ring structure including an opening 230o or a gap 230o. The opening 230o may define an opening width (e.g. a gap width) of the capacitive structure 230. The opening width may correspond to the distance between the portions of the capacitive structure 230 adjacent to the opening 230o. The opening 230o may provide a region (e.g. a passage), through which leads, embedded in the semiconductor body 102 (or other embedded circuit structures), may extend into the semiconductor body region 111 from outside the semiconductor body region 111.

According to various embodiments, a region, e.g. the first or the second electrode region 230a, 230b or the capacitive structure 230, at least partially surrounding the semiconductor body region 111 may be understood as a region that includes an opening 230o, which interrupts the path, along which the region surrounds the semiconductor body region 111. The width of the opening 230o may be less than the length of the path, along which the region surrounds the semiconductor body region 111. The width of the opening 230o may be e.g. less than about 50%, e.g. less than about 25%, e.g. less than about 10% of the length of the path surrounding the semiconductor body region 111. A region at least partially surrounding the semiconductor body region 111 may further be understood as a region that includes more than one opening 230o, e.g. two, three, four, or more than four openings 230o. According to various embodiments, at least partially surrounding the semiconductor body region 111 may include the case of surrounding the semiconductor body region 111 completely.

FIG. 3A illustrates a semiconductor chip 300 according to various embodiments, in a plan view (similar to FIG. 2B and FIG. 2C). The capacitive structure 230 may be electrically coupled to a measurement circuit 310. The measurement circuit 310 may be configured to detect a chip crack propagating into the capacitive structure 230. The measurement circuit 310 may be integrated into the semiconductor chip 300, e.g. disposed in the semiconductor body region 111. Alternatively, the measurement circuit 310 may be separated from the semiconductor chip 300, e.g. the measurement circuit 310 may be part of a discrete circuit, e.g. part of an external chip electrically coupled with the semiconductor chip 300, e.g. a detection unit or a measurement device 310 (also called a monitoring unit or watchdog).

The capacitive structure 230 may include a first electrode region 230a, a second electrode region 230b and an electrically insulating region 230i between the first electrode region 230a and the second electrode region 230b (not shown in FIG. 3A, see e.g. FIG. 2A to FIG. 2C). According to various embodiments, the measurement circuit 310 may be configured to electrically analyze the capacitive structure 230, e.g. measuring the dielectric strength of the capacitive structure 230 or the leakage current of the capacitive structure 230, in other words, between the first electrode region 230a and the second electrode region 230b. Therefore, the measurement circuit 310 may be configured to apply a voltage between the first electrode region 230a and the second electrode region 230b and measure a characteristic variable of the capacitive structure, e.g. a current between the first electrode region 230a and the second electrode region 230b, the current corresponding to the voltage. The measurement circuit 310 may be further configured to identify a chip crack propagating into the capacitive structure 230 or the semiconductor body region 111 based on the measured current.

Alternatively, according to various embodiments, the measurement circuit 310 may be configured to apply a current between the first electrode region 230a and the second electrode region 230b (e.g. a bias current) and measure a characteristic variable of the capacitive structure 230, e.g. a voltage between the first electrode region 230a and the second electrode region 230b, the voltage corresponding to the current. The measurement circuit 310 may be further configured to identify a chip crack propagating into the capacitive structure 230 or the semiconductor body region 111 based on the measured voltage.

In other words, the measurement circuit 310 may be configured to measure a value of the characteristic variable of the capacitive structure 230 by electrically characterizing the capacitive structure 230. Furthermore, the measurement circuit 310 may be configured to determine a crack based on the measured value of the characteristic variable.

A measurement circuit 310 layout, according to various embodiments is exemplarily shown in FIG. 3A. Apart from the measurement circuit 310 illustrated in FIG. 3A, other measurement circuit 310 layouts may be used to electrically characterize the capacitive structure 230.

As illustrated in FIG. 3A, a measurement circuit 310 may include a first connector 310a, which may be electrically coupled to the first electrode region 230a, and a second connector 310b, which may be electrically coupled to the second electrode region 230b. Alternatively, the first connector 310a may be electrically coupled to the second electrode region 230b and the second connector 310b may be electrically coupled to the first electrode region 230a. Furthermore, the measurement circuit 310 may include a voltage source 312b, a comparator 316, and additional circuit components 314 (e.g. a resistor, a capacitor, a diode, an inductor, or other electrical components).

According to various embodiments, the measurement circuit 310 may be configured to apply a bias voltage between the first electrode region 230a and the second electrode region 230b. Therefore, the first connector 310a may be coupled to the voltage source 312b (e.g. for supplying the bias voltage) and the second connector 310b may be coupled to electrical ground.

Further, the first connector 310a may be coupled to a first input of the comparator 316. The comparator 316 may be configured to compare an electrical voltage coupled to the first input of the comparator 316 with a reference voltage 312r coupled to a second input of the comparator 316. The comparator 316 may further be configured to output a first signal if a voltage difference between the first and the second input of the comparator 316 is greater than a predetermined difference and to output a second signal if the voltage difference between the first and the second input of the comparator 316 is less than the predetermined difference.

A chip crack propagating into the capacitive structure 230 may change, for example, the dielectric strength of the electrically insulating region 230i resulting in a change of the voltage difference between the first and the second input of the comparator 316. In response to the chip crack propagating into the capacitive structure 230, the measurement circuit 310 may output the first signal, which may be further processed (or computed) to change the operation mode of the semiconductor chip 300. The additional circuit components 314 may be configured to tune the detection behavior (also called output behavior) of the measurement circuit 310, e.g. a detection time, detection delay or a detection sensitivity.

According to various embodiments, the first signal and the second signal may be part of a watchdog signal, which the measurement circuit 310 may provide. The watchdog signal may be further processed (or computed) to control (e.g. change) the operation mode of the semiconductor chip 300.

Figure 7A:
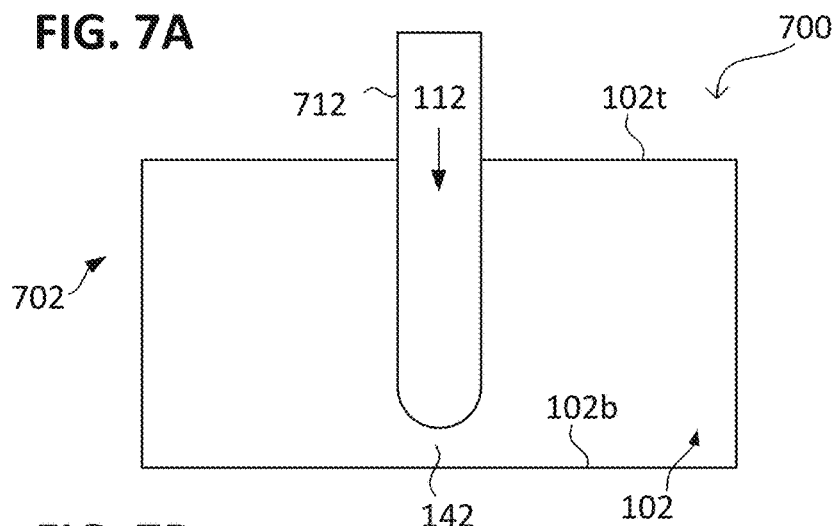
FIG. 7A to FIG. 7C respectively show a semiconductor chip at various stages during processing according to various embodiments.

According to various embodiments, a semiconductor chip may be part of a wafer 702, wherein the semiconductor chip may be surrounded by a kerf region 142 (in a lateral direction) of the wafer 702 (not shown, see for example semiconductor chip 700 in FIG. 7A). In the kerf region 142, the wafer 702 may be designated to be cut, e.g. sawed, milled, diced, etc., to singulate the semiconductor chip from the wafer 702 (e.g. see FIG. 7A). For detection of chip cracks generated during singulation of the semiconductor chip from the wafer 702, the capacitive structure 230 may be disposed between the kerf region 142 and the semiconductor body region 111 of the semiconductor chip.

According to various embodiments, the capacitive structure 230 may be disposed between the kerf region 142 and the seal ring 120 of the semiconductor chip, as illustrated in FIG. 3A. Alternatively, according to various embodiments, the capacitive structure 230 may be disposed between the seal ring 120 of the semiconductor chip and the semiconductor body region 111 of the semiconductor chip.

FIG. 3B illustrates a semiconductor chip 350, according to various embodiments, in a plan view (similar to FIG. 2B and FIG. 2C), wherein the semiconductor chip 350 may include an additional capacitive structure 330, which may at least partially surround an additional semiconductor body region 311 of the semiconductor chip 350 in a lateral direction. In one or more embodiments, the additional semiconductor body region 311 may be surrounded by the semiconductor body region 111.

Similarly, according to various embodiments, a semiconductor chip may include a plurality of capacitive structures, wherein each capacitive structure of the plurality of capacitive structures may at least partially surround at least one semiconductor body region.

According to various embodiments, a first capacitive structure (e.g. 230) of the plurality of capacitive structures may surround a second capacitive structure (e.g. 330) of the plurality of capacitive structures, as exemplarily illustrated in FIG. 3B. Alternatively, according to various embodiments, the first capacitive structure (e.g. 230) of the plurality of capacitive structures and the second capacitive structure (e.g. 330) of the plurality of capacitive structures may be disposed side by side.

FIG. 4A to FIG. 4F respectively illustrate a semiconductor chip 400 in a cross sectional view, e.g. in a cross sectional view taken along line 201 or in a similar cross sectional view as a cross sectional view taken along line 201 or 301, during processing the semiconductor chip 400, e.g. during a method for forming a capacitive structure 230 according to various embodiments.

Figure 4A:
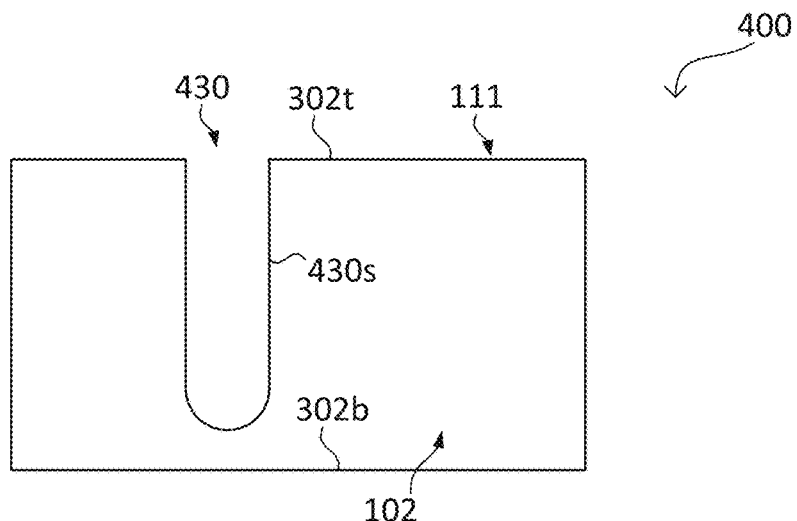

FIG. 4A illustrates the semiconductor chip 400 in a cross sectional view at a processing stag. For example, according to various embodiments, the semiconductor chip 400 may be a semiconductor chip at an initial processing stage, the semiconductor chip 400 designated for forming an integrated circuit structure in the semiconductor chip 400 (e.g. in a semiconductor body region 111). Alternatively, according to various embodiments, the semiconductor chip 400 may be a completely processed semiconductor chip including an integrated circuit structure. For example, the semiconductor chip 400 may be a part of a wafer 702 and may be designated to be separated from the wafer 702 or the semiconductor chip 400 may be a part a wafer level package.

The semiconductor chip 400 may include a semiconductor body 102 with a semiconductor body region 111. According to various embodiments, at least one trench 430, e.g. a blind trench 430 (in analogy to a blind hole), may be formed in the semiconductor body 102 adjacent to the semiconductor body region 111. The trench 430 may define a sidewall 430s on the semiconductor body region 111.

The trench 430 may be formed such that the trench 430 may extend from the first surface 302t (e.g. a top surface) of the semiconductor chip 400 into the semiconductor body 102. In other words, the trench 430 may be formed such that the trench 430 may extend vertically into the semiconductor body 102. The trench 430 may be formed by performing any known method from semiconductor technology, e.g. by etching or sawing. The trench 430 may be formed to extend into a bottom portion of the semiconductor body region 111 (also called a deep trench). For example, the trench 430 may be formed to extend through at least 50% of the thickness of the semiconductor body 102, e.g. at least 60%, e.g. at least 70%, e.g. at least 80%, e.g. at least 90%.

According to various embodiments, the trench 430 may at least substantially extend from the first surface 302t of the semiconductor body 102 to a second surface 302b of the semiconductor body 102, the second surface 302b being opposite the first surface 302t. The trench 430 may be formed without breaking through to the second surface 302b. The trench 430 may be formed such that the trench 430 may at least partially surround the semiconductor body region 111 of the semiconductor chip 400.

Figure 4B:
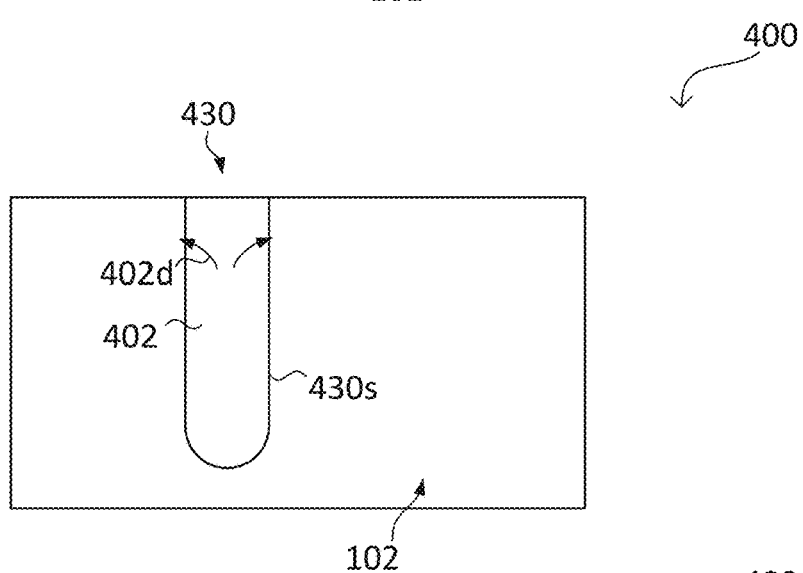

According to various embodiments, a dopant material 402 (which may operate as dopant donor) may be disposed in the trench 430. The dopant material 402 may be disposed such that the sidewall 430s may at least substantially be covered with the dopant material. For example, the trench 430 may at least substantially be filled with the dopant material 402, as illustrated in FIG. 4B.

According to various embodiments, "at least substantially filled" may be understood as meaning that a portion of an inner volume of a cavity, a recess or a trench is filled with a material, e.g. more than about 70% of the inner volume, e.g. more than about 80%, e.g. more than about 90%, e.g. about 100%.

The dopant material 402 may include a dopant (also called a doping agent). According to various embodiments, if the sidewall 430s includes a group IV semiconductor (e.g. silicon or germanium), the dopant material 402 may include a group III element (p-type dopant) or a group V element (n-type dopant), for example a chemical element from the following group of chemical elements: boron, arsenic, phosphorus, antimony, aluminum or gallium. Alternatively, according to various embodiments, if the sidewall 430s includes a III-V compound semiconductor (e.g. gallium arsenide), the dopant material 402 may include a chemical element from the following group of chemical elements: sulfur, selenium, tellurium, silicon, germanium, magnesium, zinc, cadmium. For example, the dopant material 402 may include a glass (e.g. a boron glass) including boron as dopant.

Figure 4C:
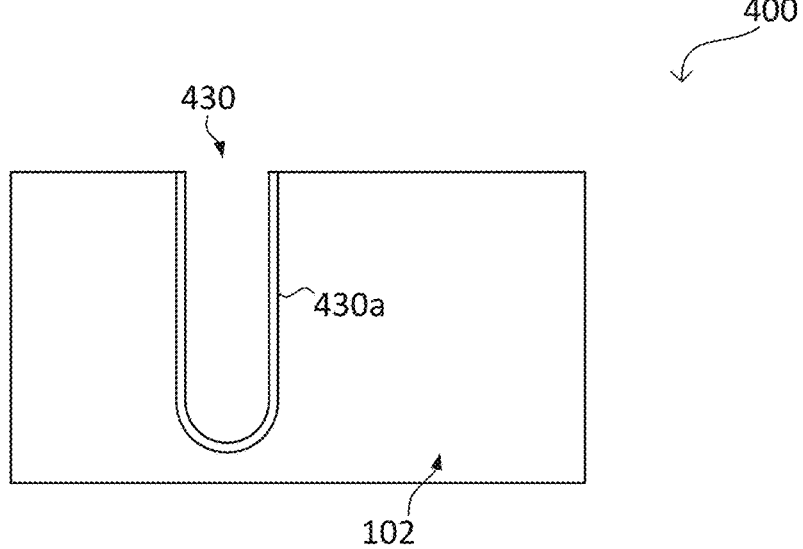

The dopant may be configured to alter the electrical properties of the sidewall 430s, e.g. insert charge carriers into the sidewall 430s, if the dopant is introduced into the sidewall 430s. The dopant may be configured to dope at least the sidewall 430s to form a first doping type semiconductor 430a (also referred as first semiconductor region 430a of a first conductivity type), e.g. an n-type semiconductor or a p-type semiconductor, in other words, to form a doped sidewall 430a from the sidewall 430s, as illustrated in FIG. 4C. In other words, the dopant may be configured to dope at least the sidewall 430s to form a first semiconductor region 430a of a first conductivity type from the sidewall 430s.

For example, the dopant material 402 may be annealed to introduce the dopant into the sidewall 430s, e.g. by temperature induced diffusion 402d (also called outdiffusing) of the dopant into the sidewall 403s. After introducing the dopant into the sidewall 430s, the dopant material 402 may be removed, e.g. to expose the doped sidewall 430a. The doped sidewall 430a may be part of the first electrode region 230a.

Alternatively, forming the first doping type semiconductor 430a may include implanting a dopant into the first electrode region 230a, e.g. by ion implantation or other known doping methods.

Further, a filling material 432, e.g. a polycrystalline semiconductor, e.g. polycrystalline silicon, or another electrically conductive material, e.g. a metal or a metal alloy, may be disposed into the trench 430, as illustrated in FIG. 4D. The filling material 432 may be configured to electrically contact the doped sidewall 430a. The filling material 432 may be part of the first electrode region 230a.

Further, a second doping type semiconductor 430b, e.g. an n-type semiconductor or a p-type semiconductor (also referred as second semiconductor region 430b of a second conductivity type), next to, e.g. adjacent to, the first doping type semiconductor 430a may be formed, as illustrated in FIG. 4E. Forming the second doping type semiconductor 430b may include forming a trench and doping a sidewall of the trench, similar to the first doping type semiconductor 430a. Alternatively, forming the second doping type semiconductor 430b may include implanting a dopant into the second electrode region 230b, e.g. by ion implantation or other known doping methods. According to various embodiments, the second doping type semiconductor 430b may be a part of the second electrode region 230b.

According to various embodiments, the second doping type semiconductor 430b may be configured such that the first doping type semiconductor 430a and the second doping type semiconductor 430b provide a p-n-junction. For example, the first doping type semiconductor 430a may include p-type doped silicon and the second doping type semiconductor 430b may include n-type doped silicon. The first doping type semiconductor 430a and the second doping type semiconductor 430b may form a depletion region between them (or at their interface region). The depletion region may form or may be part of the electrically insulating region 230i and may electrically insulate the first doping type semiconductor 430a from the second doping type semiconductor 430b.

A crack propagating into the depletion region (electrically insulating region 230i) may cause a shortcut (electrical shortcut) between the first doping type semiconductor 430a and the second doping type semiconductor 430b or may cause an increase of the leakage current of the p-n-junction.

Illustratively, according to various embodiments, the first doping type semiconductor 430a may be part of a first semiconductor electrode 230a (of a first conductivity type) and the second doping type semiconductor 430b may be part of a second semiconductor electrode 230b (of a second conductivity type).

Further, a first contact pad 434a may be formed, e.g. deposited on the first doping type semiconductor 430a, as illustrated in FIG. 4F. The first contact pad 434a may electrically contact the first doping type semiconductor 430a. Similarly, a second contact pad 434b may be formed, the second contact pad 434b may electrically contact the second doping type semiconductor 430b. The first contact pad 434a and the second contact pad 434b may include an electrically conductive material (e.g. a metal or a metal alloy) or a metalized semiconductor. According to various embodiments, forming the first contact pad 434a and the second contact pad 434b may include disposing, e.g. depositing, e.g. plating, a metal or a metal alloy.

During processing the semiconductor chip 400, the semiconductor body 102 of the semiconductor chip 400 may be thinned, e.g. to level 450, e.g. by abrasive machining (e.g. grinding) or chemical machining (e.g. etching). Thinning may be performed e.g. if the thickness of the semiconductor body 102 is greater than the (intended) thickness of the completely processed semiconductor chip 400. The thickness of the semiconductor body 102, e.g. before thinning, may be understood as a vertical extension of the semiconductor body 102, e.g. a distance from the first surface 302t of the semiconductor body 102 to the second surface 302b of the semiconductor body 102. After thinning, the thickness may be reduced and may correspond, for example, to a distance from the first surface 302t to the surface 302b' (or level 450).

According to various embodiments, the thickness of the semiconductor body 102, e.g. before thinning the semiconductor chip 400, may be in the range from about several hundreds of micrometers to about several thousands of micrometers, e.g. in the range from about 100 µm to about 5 mm, e.g. the thickness of the semiconductor body 102 may be in the range from about 200 µm to about 1 mm, e.g. in the range from about 300 µm to about 800 mm.

According to various embodiments, the semiconductor chip 400 may be thinned after forming the capacitive structure 230. According to various embodiments, thinning the semiconductor chip 400 may provide the bottom side of the semiconductor body region 111 or the completely processed semiconductor chip 400. For example, after thinning, the surface 302b' may include or correspond to the bottom side 102b of the semiconductor body region 111.

According to various embodiments, the depth of the trench 430 and the corresponding depth or vertical extension of the capacitive structure 230 (e.g. the first electrode region 230a or the second electrode region 230b) may be in the range from about several micrometers to about several hundreds of micrometers, e.g. in the range from about 5 µm to about 500 µm, e.g. less than about 400 µm, e.g. less than about 100 µm, e.g. less than about 50 µm. Illustratively, the capacitive structure 230 may be formed such that by thinning the semiconductor chip 400 the capacitive structure 230 may break through the second surface 302b'.

According to various embodiments, the thickness of the semiconductor body region 111, e.g. after thinning the semiconductor chip 400, may be in the range from about several micrometers to about several hundreds of micrometers, e.g. in the range from about 5 µm to about 500 µm, e.g. the thickness of the semiconductor body region 111 may be less than about 400 µm, e.g. less than about 100 µm, e.g. less than about 50 µm.

According to various embodiments, the second surface 302b of the semiconductor body 102 may provide the second surface 102b of the semiconductor body region 111, e.g. if the semiconductor body 102 is already thinned or no thinning of the semiconductor body 102 is performed. In other words, the thickness of the semiconductor body 102 may be the thickness of the completely processed semiconductor chip 400.

Figure 5A:
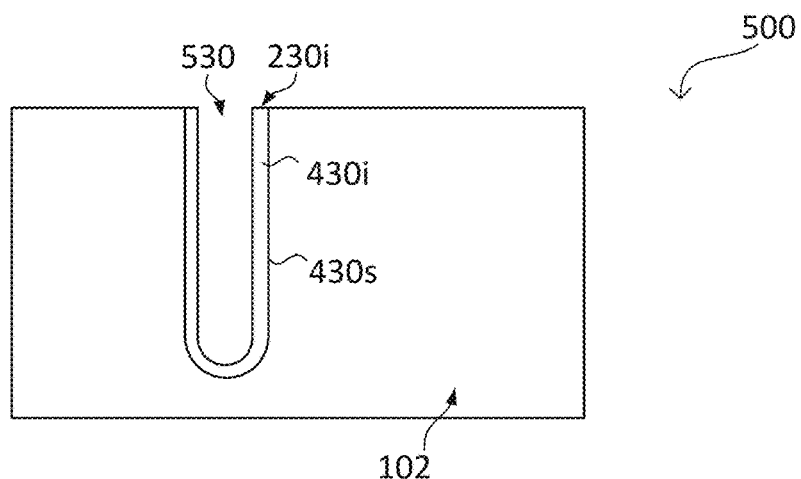
FIG. 5A to FIG. 5C respectively show a semiconductor chip at various stages during processing according to various embodiments.
Figure 5B:
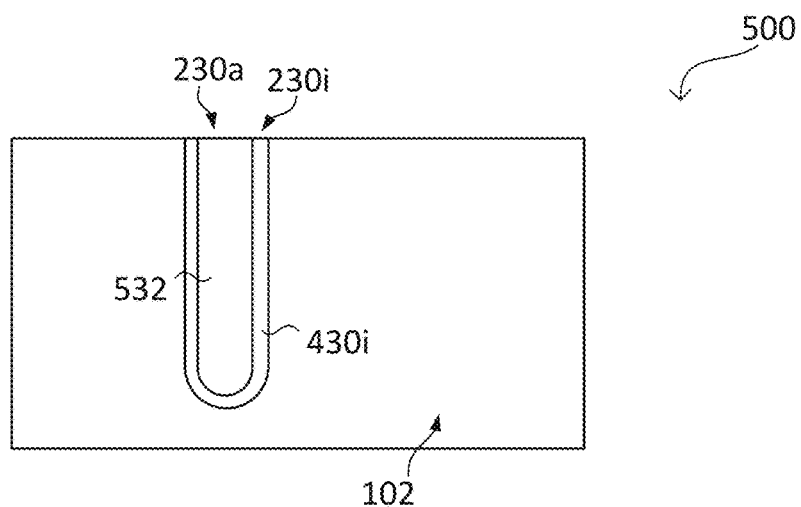
Figure 5C:
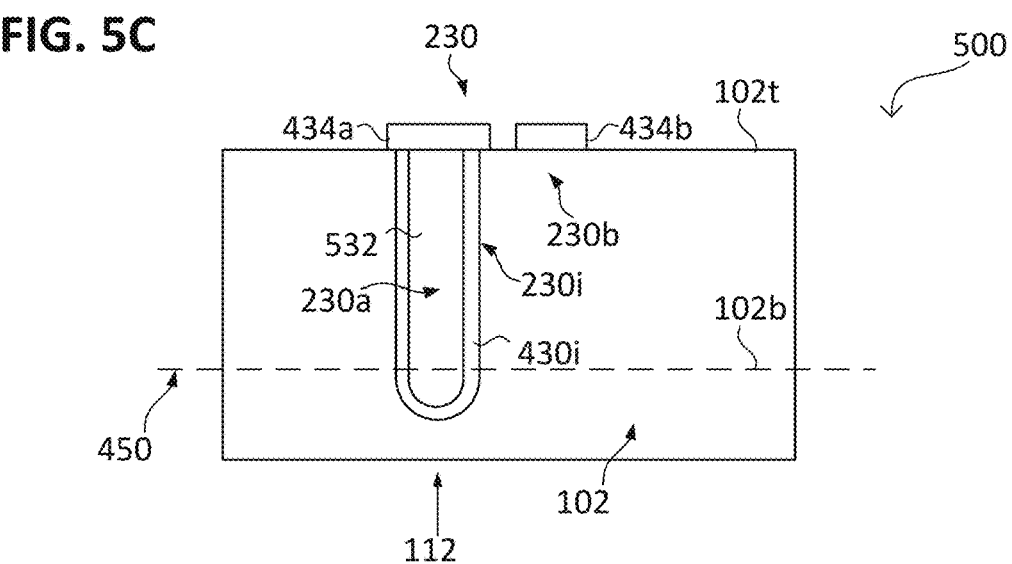

FIG. 5A to FIG. 5C respectively illustrate a semiconductor chip 500 in a cross sectional view, e.g. in a similar cross sectional view as a cross sectional view taken along line 201 or 301, during processing the semiconductor chip 500, e.g. during a method for forming a capacitive structure 230 according to various embodiments.

A trench 430 may be formed in a semiconductor body 102 (not shown, see FIG. 4A). According to various embodiments, an electrically insulating material 430i may be disposed in the trench 430 after forming the trench 430, as illustrated in FIG. 5A. The electrically insulating material 430i may be part of the electrically insulating region 230i. The electrically insulating material 430i may be disposed such that the sidewall 430s of the trench 430 may at least substantially be covered by the electrically insulating material 430i (e.g. completely covered). The electrically insulating material 430i may be disposed such that a recess 530 is provided in the electrically insulating material 430i.

Alternatively, according to various embodiments, the electrically insulating material 430i may be formed from the sidewall 430s of the trench, e.g. by forming an oxide (by oxidizing) or by forming a nitride from the sidewall 430s of the trench.

According to various embodiments, an electrically conductive material 532 may be disposed in the recess 530, e.g. a metal, metal alloy or polycrystalline silicon (as shown in FIG. 5B). The electrically conductive material 532 may be part of the first electrode region 230a (also referred as metal electrode 230a) in some embodiments.

Further, a first contact pad 434a may be formed, e.g. deposited on the conductive material 532, as illustrated in FIG. 5C. The first contact pad 434a may electrically contact the conductive material 532 (for example, the metal electrode 230a). A second contact pad 434b may be formed on the semiconductor body 102. The second contact pad 434b may electrically contact the semiconductor body 102. The semiconductor body 102 electrically contacted by the second contact pad 434b may be part of the second electrode region 230b (also referred as semiconductor electrode 230b). According to various embodiments, the semiconductor body 102 may include a doped semiconducting material, e.g. an n-type semiconductor or a p-type semiconductor, which is contacted by the second contact pad 434b.

In other words, the first electrode region 230a may include a metal or metal alloy (to provide a metal electrode 230a) and the second electrode region 230b may include a doped semiconductor, e.g. p-type doped silicon (to provide a semiconductor electrode). According to various embodiments, the semiconductor electrode 230b may be formed from a doped portion of the semiconductor body region 111.

Figure 6A:
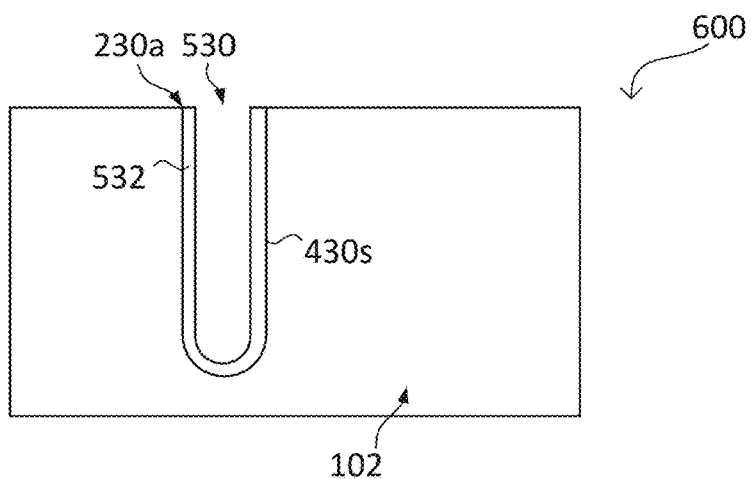
FIG. 6A to FIG. 6C respectively show a semiconductor chip at various stages during processing according to various embodiments.
Figure 6B:
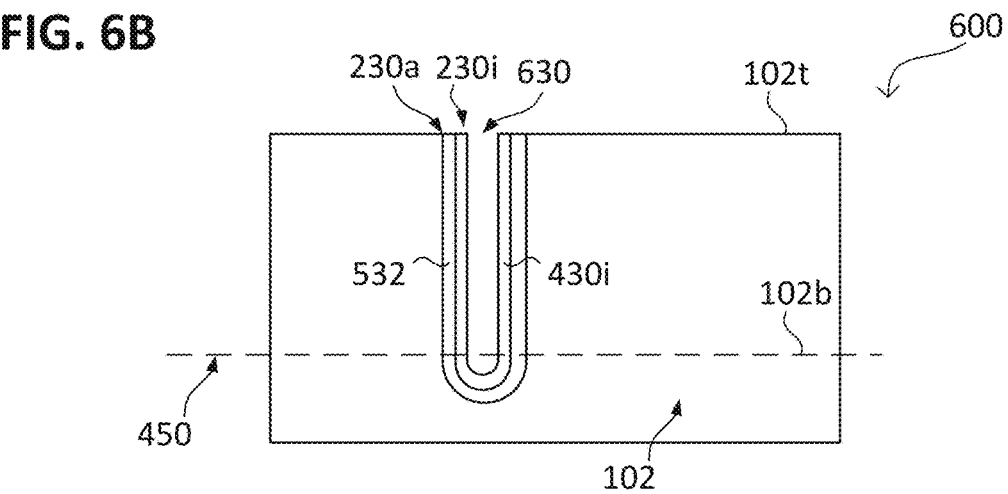
Figure 6C:
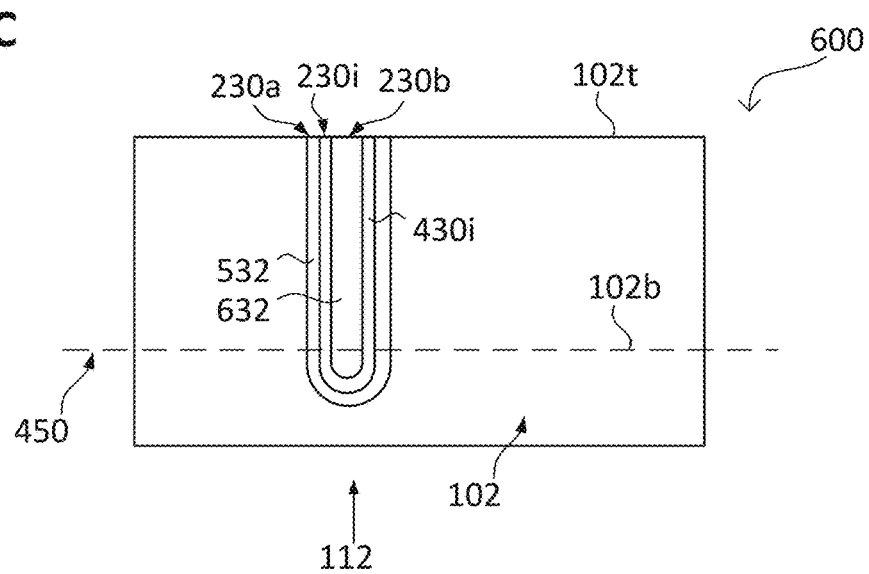

FIG. 6A to FIG. 6C respectively illustrate a semiconductor chip 600 in a cross sectional view, e.g. in a similar cross sectional view as a cross sectional view taken along line 201 or 301, during processing the semiconductor chip 600, e.g. during a method for forming a capacitive structure 230 according to various embodiments.

A trench 430 may be formed in a semiconductor body 102 (not shown, see FIG. 4A). According to various embodiments, a first electrically conductive material 532 may be disposed in the trench 430 after forming the trench 430, as illustrated in FIG. 6A. The first electrically conductive material 532 may be part of the first electrode region 230a. The first electrically conductive material 532 may be disposed such that the sidewall 430s of the trench 430 may at least substantially be covered by the first electrically conductive material 532 (e.g. completely covered). The first electrically conductive material 532 may be disposed such that a recess 530 is provided in the first electrically conductive material 532. The first electrically conductive material 532 may be part of a first metal electrode 230a.

Further, an electrically insulating material 430i may be disposed in the recess 530, as illustrated in FIG. 6B. The electrically insulating material 430i may be part of the electrically insulating region 230i. The electrically insulating material 430i may be disposed such that the first electrically conductive material 532 may at least substantially be covered by the electrically insulating material 430i (e.g. completely covered). The electrically insulating material 430i may be disposed such that a further recess 630 is provided in the electrically insulating material 430i.

Figure 7B:
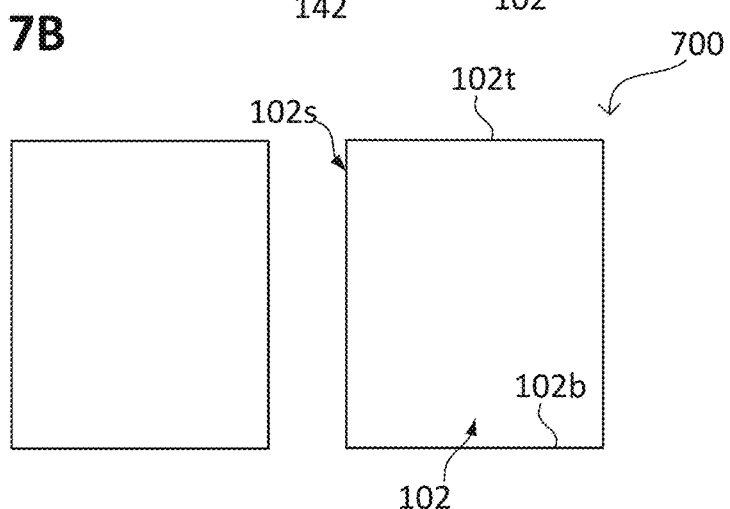
Figure 7C:
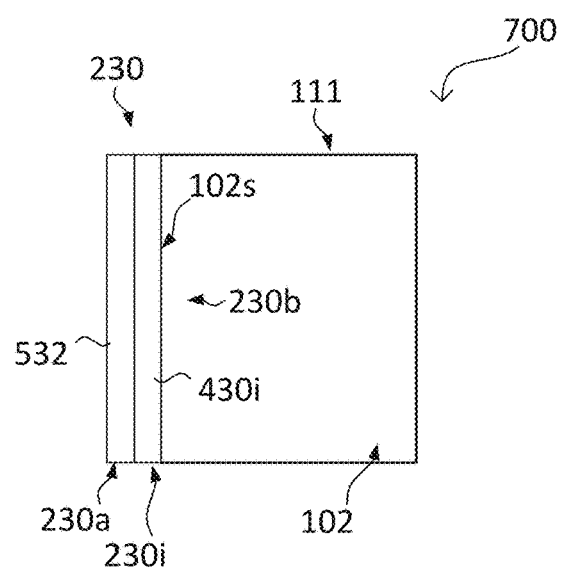

According to various embodiments, the semiconductor body 102 may be thinned, e.g. to a level 450, as described herein, wherein the further recess 630 in the electrically insulating material 430i may separate the semiconductor body 102 into two portions (which may form two separated semiconductor body regions 111, one of the two separated semiconductor body regions 111 may be provided as illustrated in FIG. 7C), each of the two portions including a capacitive structure 230.

In another embodiment, a second electrically conductive material 632 may be disposed in the recess 630, as illustrated in FIG. 6C. The second electrically conductive material 632 may be part of the second electrode region 230b (also referred as second metal electrode 230b in some embodiments). The second electrically conductive material 632 may be disposed such that the electrically insulating material 430i may at least substantially be covered by the second electrically conductive material 632 (e.g. completely covered, e.g. by substantially filling the recess 630). The semiconductor body 102 may be thinned, e.g. to a level 450, to provide the bottom surface 102b of the semiconductor body region 111. According to various embodiments, the second electrode region 230b may substantially extend from the first surface 102t to the second surface 102b, as illustrated in FIG. 6C.

Further, the first electrically conductive material 532 and the second electrically conductive material 632 each may be electrically coupled to a contact pad, as described herein. According to various embodiments, the first electrode region 230a may include a first metal or first metal alloy (to provide a first metal electrode 230a) and the second electrode region 230b may include a second metal or second metal alloy (to provide a second metal electrode 230b).

FIG. 7A to FIG. 7C respectively illustrate a semiconductor chip 700 in a cross sectional view, e.g. in a similar cross sectional view as a cross sectional view taken along line 201 or 301, during processing the semiconductor chip 700, e.g. during a method for singulating semiconductor chip 700 from a wafer 702 and forming a capacitive structure 230 according to various embodiments.

For the singulation of the semiconductor chip 700 from a wafer 702, a known wafer dicing process 112 may be carried out in the kerf region 142, e.g. a mechanical wafer dicing process 112, e.g. mechanical sawing (e.g. using a dicing saw 712), as illustrated in FIG. 7A, or other wafer dicing processes 112 (e.g. laser cutting).

After the wafer dicing process 112, the semiconductor body 102 of the semiconductor chip 700 may include a sidewall 102s (lateral side 102s) extending between the top side 102t and the bottom side 102b of the semiconductor body 102, as illustrated in FIG. 7B. Due to wafer dicing process 112, a chip crack 110 may occur, e.g. the chip crack 110 emanating from the sidewall 102s of the semiconductor chip 700.

According to various embodiments, a capacitive structure 230 may be formed on the sidewall 102s of the semiconductor chip 700, as illustrated in FIG. 7C. The capacitive structure 230 may provide the detection of chip cracks 110 already being present in the semiconductor chip 700 after sawing 112, and also the detection of chip cracks 110 occurring during operation of the completely processed semiconductor chip 700, e.g. in an electrical device.

In other words, the capacitive structure 230 formed on the sidewall 102s of the semiconductor chip 700 may detect a potentially existent chip crack 110 in the sidewall 102s. The chip crack 110 may impair, e.g. shunt, the capacitive structure 230 as formed or the chip crack 110 may impair the capacitive structure 230 if the chip crack 110 continues propagating into the semiconductor chip 700.

To form the capacitive structure 230, according to various embodiments, an electrically insulating material 430i may be formed (e.g. deposited) on the sidewall 102s such that the sidewall 102s (lateral side 102s) may at least substantially be covered by the electrically insulating material 430i (e.g. completely covered). Alternatively, the sidewall 102s of the semiconductor chip 700 may be oxidized to form a semiconductor oxide layer. The term "substantially covered" may be understood as meaning that an area, e.g. the surface of the sidewall 102s or a surface of a trench 430 may be covered to more than 80%, e.g. more than 90%, e.g. completely covered. Illustratively, the electrically insulating material 430i may form an electrically insulating layer 230i over the sidewall 102s, wherein the electrically insulating material 430i may provide the electrically insulating region 230i of the capacitive structure 230.

Further, an electrically conductive material 532 (e.g. forming a metal electrode 230a) may be disposed (e.g. deposited) over the electrically insulating material 430i such that electrically insulating material 430i may at least substantially be covered by the electrically conductive material 532 (e.g. completely covered). Illustratively, the electrically conductive material 532 may form an electrically conductive layer over the electrically insulating layer 230i. The electrically conductive material 532 may provide the first electrode region 230a of the capacitive structure 230.

In some embodiments, the capacitive structure 230 may include a metal electrode 230a over the lateral side 102s and an electrically insulating layer 230i disposed between the metal electrode 230a and the lateral side 102s.

According to various embodiments, a first electrical contact pad 434a may be formed, the first electrical contact pad 434a electrically contacting the metal electrode 230a (in other words, the electrically conductive material 532) and a second electrical contact pad 434b may be formed, the second electrical contact pad 434b electrically contacting a portion of the semiconductor body 102, e.g. a doped portion of the semiconductor body region 111, as described herein. The doped portion of the semiconductor body region 111 may provide a semiconductor electrode 230b, as described herein.

The electrically conductive material 532 may include a material that is able to flow (or creep, e.g. by plastic deformation of the material) into a chip crack 110 by means of capillary flow, such that the material electrically contacts a portion the semiconductor body 102 (or the semiconductor body region 111) adjacent to the chip crack 110. Capillary flow or capillary motion may be understood as the ability of the material 532 to flow into narrow spaces by means of capillary forces without the assistance of, and also in opposition to, external forces like gravity. For example, capillary flow may be due to cohesion and adhesion, which cause the material 532 to move into a chip crack 110.

If a chip crack 110 propagates into the electrically insulating material 430i or a chip crack 110 is already present when the electrically insulating material 430i is formed, the chip crack 110 may cause an opening of the electrically insulating material 430i (in other words, the opening in the electrically insulating material 430i may expose a portion of the sidewall 102s). The material 532 may move into the opening in the electrically insulating material 430i by means of capillary flow and may electrically contact the semiconductor electrode 230b (or the semiconductor body region 111). Therefore, the semiconductor electrode 230b may be shunted to the electrically conductive material 532.

In another embodiment, a semiconductor chip 700, illustrated in FIG. 7C, may be provided by thinning 450 a semiconductor body 102, as illustrated in FIG. 5C, and optionally separating 112, e.g. by dicing, the semiconductor body 102 through the first electrode region 230a. In other words, the sidewall 430s of the trench 430 may form a sidewall of the semiconductor body 102 after separating 112 the semiconductor body 102.

FIG. 8A illustrates a semiconductor chip 800, according to various embodiments, in a cross sectional view (similar to FIG. 2A or FIG. 7C). The semiconductor chip 800 may include a capacitive structure 230 for detecting crack propagation into the semiconductor chip 800. To provide a semiconductor chip 800 with a capacitive structure 230, as illustrated in FIG. 8A, various methods of processing the semiconductor chip 800 may be carried out, as described herein.

According to various embodiments, the semiconductor chip 800, as illustrated in FIG. 8A, may be provided by thinning 450 a semiconductor body 102, as illustrated in FIG. 6C, and optionally separating 112, e.g. by dicing, the semiconductor body 102 through the second electrically conducting material 632. In other words, the sidewall 430s of the trench 430 may form a sidewall of the semiconductor body 102 after separating 112 the semiconductor body 102.

According to various embodiments, the semiconductor chip 800, as illustrated in FIG. 8A, may be provided by disposing a second electrically conducting material 632 between the sidewall 102s of a semiconductor body 102, as illustrated in FIG. 7C, and the electrically insulating layer 430i.

The capacitive structure 230 may include two electrodes 230a, 230b (in other words, two electrode regions 230a, 230b) separated (e.g. electrically insulated) by a separation layer 230i (in other words, an electrically insulating layer 230i). The capacitive structure 230 may be disposed at the transition region between the semiconductor chip 800 and the kerf region 142 (also called sawing frame 142). The two electrodes 230a, 230b may surround the semiconductor body region 111 of the semiconductor chip 800 completely and may extend from the top side 102t to the bottom side 102b of the semiconductor chip 800.

A chip crack 110 emanating from the sidewall of the semiconductor chip 800 (which may be located next to the sawing frame 142) may propagate through the capacitive structure 230 (also referred as perimeter area 230). The chip crack 110 propagating through the capacitive structure 230 may damage or destroy the separation layer 230i, which may be detected by an electrical characterization of the capacitive structure 230, e.g. by a measurement circuit, e.g. measurement circuit 310 of FIG. 3A. The electrical characterization (e.g. providing a so-called failure mapping) may define characteristical failure symptoms, e.g. a shortcut, a changed (e.g. increased) leakage current or a changed (e.g. reduced) dielectric strength of the capacitive structure 230. Occurrence of one or more of the characteristical failure symptoms may correlate with the propagation of chip cracks 110 and may enable to initiate appropriate countermeasures, e.g. changing the mode of operation of the semiconductor chip 800 to avoid an undefined behavior of the semiconductor chip 800.

According to various embodiments, the semiconductor chip 800 may be disposed (e.g. attached, e.g. glued or soldered) on a lead frame 802 for further processing the semiconductor chip 800, e.g. the lead frame 802 may electrically contact the semiconductor chip 800. The lead frame 802 may include a metal structure (or a metal alloy structure) or a contact structure, which may be configured to transmit signals to or from the semiconductor chip 800. For example, if the completely processed semiconductor chip 800 is encapsulated in a chip package, the lead frame 802 may provide the transmission of signals between the outside of a chip package (e.g. a connection pad of the chip package) and the semiconductor chip 800.

The bottom side 102b of the semiconductor body region 111 may be defined by the bottom surface of the completely processed semiconductor chip 800 which may be attached to the lead frame 802.

According to various embodiments, the electrically insulating layer 230i may include a viscous material. The viscous material may be configured to leak through an opening in an electrode region 230a, 230b (also simply referred as electrode 230a, 230b). The opening in the electrode 230a, 230b may be caused by a chip crack 110. In other words, the viscous material may exhibit shear flow or any other deformation linearly with time when stress or a force, e.g. by gravitation, is applied to the viscous material. The viscous material may leak through the opening in the electrode 230a, 230b which may change the electric properties (e.g. the dielectric strength) of the capacitive structure 230 (e.g. between the electrodes 230a, 230b adjacent to the viscous material). The viscous material may include a paste like material, a gel like material, a grease, a liquid material, or a mixture of a solid material and a liquid material. For example, the viscous material may include a glass, a polymer, or an oil.

FIG. 8B illustrates a semiconductor chip 850, according to various embodiments, in a cross sectional view (analog to FIG. 2A or FIG. 6C). The semiconductor chip 850 may include a capacitive structure 230 with a plurality of electrode regions 230a, 230b, . . . , 230f (also referred as a plurality of electrodes 230a, 230b, . . . , 230f) and a plurality of electrically insulating layers 230i.

According to various embodiments, the semiconductor chip 850 may be part of a wafer, wherein the semiconductor chip 850 may be destined for being singulated from the wafer 702 (e.g. by cutting the wafer. e.g. by sawing the wafer). Illustratively, the wafer 702 may be cut in the kerf region 142 for singulating the semiconductor chip 850.

According to various embodiments, a capacitive structure 230 with a plurality of electrode regions 230a, 230b, . . . , 230f may be provided in the kerf region 142 of the wafer 702 before cutting the wafer 702. Six electrode regions 230a, 230b, 230c, 230d, 230e, 230f are shown as an example in FIG. 8B. However, the number of electrode regions may be different from six. The capacitive structure 230 may be provided such that the wafer 702 may be cut, e.g. sawed 112, through the capacitive structure 230, wherein at least two electrode regions, e.g. 230a and 230b, separated by an electrically insulating layer 230i, may remain attached to the semiconductor chip 850, as illustrated in FIG. 8B.

According to various embodiments, a method of processing a wafer 702, e.g. forming the capacitive structure 230 with a plurality of electrode regions 230a, 230b, . . . , 230f, may include forming a trench 430 adjacent to the semiconductor chip 850 of the wafer 702. The trench 430 may be formed in the kerf region 142. The trench 430 may substantially extend from a first surface 102t of the wafer 702 to a second surface 102b of the wafer 702 opposite the first surface 102. The first surface 102t of the wafer 702 may include the first surface 102t of the semiconductor body region 111 and the second surface 102b of the wafer 702 opposite the first surface 102 may include the second surface 102b of the semiconductor body region 111.

According to various embodiments, the method may further include forming a capacitive structure 230 in the trench 430, the capacitive structure 230 may include the plurality of electrode regions 230a, 230b, . . . , 230f, with at least a first electrode region, e.g. 230a, a second electrode region, e.g. 230b, disposed at a first side of the first electrode region, e.g. 230a and a third electrode region, e.g. 230c, disposed at a second side of the first electrode region, e.g. 230a.

Further, the capacitive structure 230 may include a first electrically insulating region 230i extending between the first electrode region, e.g. 230a, and the second electrode region, e.g. 230b, and a second electrically insulating region 230i extending between the first electrode region, e.g. 230a, and the third electrode region, e.g. 230c.

According to various embodiments, the capacitive structure 230 may be formed such that at least one of the first, the second and the third electrode regions may substantially extend from the first surface 102t of the wafer to the second surface 102b of the wafer 702 opposite the first surface 102t.

According to various embodiments, the method may further include cutting the wafer 702 through the trench 430 to singulate the semiconductor chip 850 from the wafer 702, wherein at least the first electrode region, e.g. 230a, and the second electrode region, e.g. 230b, may remain attached to the semiconductor chip 850.

In other words, the plurality of electrode regions 230a, 230b, . . . , 230f and the plurality of electrically insulating layers 230i may be disposed in the kerf region 142. The functionality of at least two electrode regions of the plurality of electrode regions 230a, 230b, . . . , 230f, according to various embodiments, as e.g. illustrated in FIG. 8B, may potentially be independent from the exact position of the sawing (or the sawing blade 712). Therefore, a chip crack 110 propagating through at least one electrically insulating layer 230i of the plurality of electrically insulating layers 230i may cause a short cut or a changed dielectric strength of the capacitive structure 230.

According to various embodiments, the semiconductor chip 850, as illustrated in FIG. 8B, may be provided by a method described herein, e.g. similar to FIG. 6A to FIG. 6C, wherein the plurality of electrode regions 230a, 230b, . . . , 230f and the plurality of electrically insulating layers 230i may be disposed in the trench 430.

According to various embodiments, the semiconductor chip 850, as illustrated in FIG. 8B may be provided, e.g. by providing a plurality of trenches, similar to the trench 430 illustrated in FIG. 4A, wherein at least one electrode region of the plurality of electrode regions 230a, 230b, . . . , 230f may be formed in one trench 430 of the plurality of trenches similar to the first electrode region 230*a*, as shown in FIG. 5C or FIG. 6C.

Figure 9A:
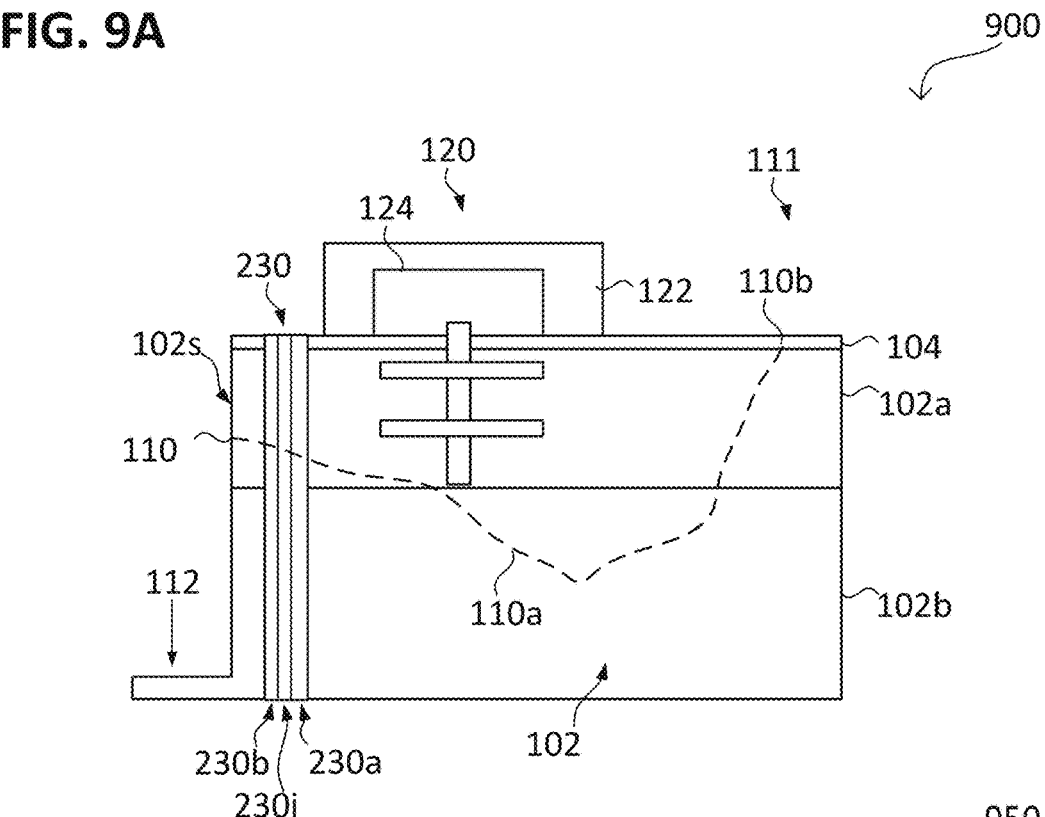
FIG. 9A and FIG. 9B respectively show a semiconductor chip according to various embodiments.

FIG. 9A illustrates a semiconductor chip 900, according to various embodiments, in a cross sectional view (similar to FIG. 1A). The semiconductor chip 900 may include a capacitive structure 230 which is disposed between the seal ring 120 and the sidewall 102*s* of the semiconductor chip 900.

Illustratively, the capacitive structure 230 functions like a plate capacitor, including two electrodes 230*a*, 230*b* (also called perimeter areas 230*a*, 230*b*). If the capacitive structure 230 is disposed at or near the sidewall 102*s* of the semiconductor chip 900, a chip crack 110 may result in an impairment of the electrically insulating region 230*i* between the two electrodes 230*a*, 230*b* (e.g. at zero hours operating time or zero hours testing time). The impairment of the electrically insulating region 230*i* may be detectable by electrical characterization of the capacitive structure 230.

According to various embodiments, on the one hand complicated stress tests, e.g. acceleration tests for early life fails, e.g. Burn-In, may not be necessary, while on the other hand a detection reliability, according to various embodiments, may be greater compared to conventional methods for detecting chip cracks 110. Furthermore, a chip crack 110 that appears during operation of a semiconductor chip 900, e.g. at a sidewall 102*s* of a semiconductor chip 900, may be identified by a capacitive structure 230 according to various embodiments.

Figure 9B:
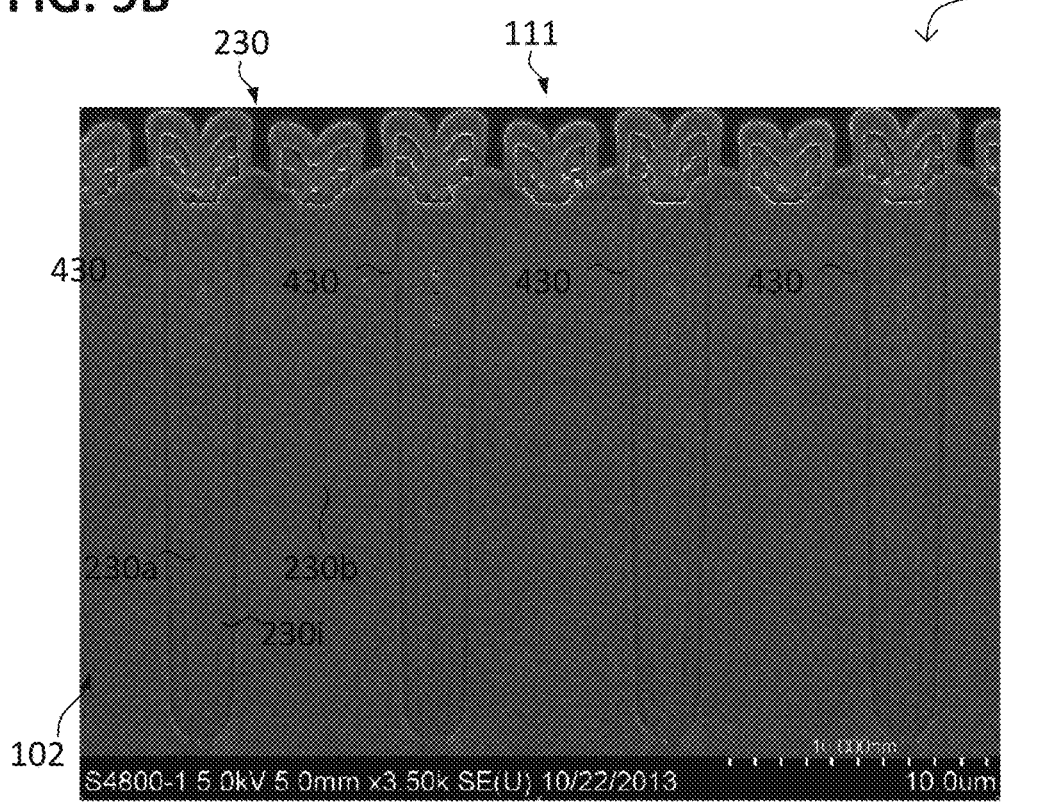

FIG. 9B illustrates a semiconductor chip 950, according to various embodiments, in a cross sectional view (similar to FIG. 1A). The semiconductor chip 950 may include a capacitive structure 230 with a plurality of trenches. In each trench 430 of the plurality of trenches, a first electrode 230*a* (e.g. a metal electrode 230*a* or a semiconductor electrode 230*a*) and an electrically insulating layer 230*i* may be disposed (similar to FIG. 5B). Further, a second electrode may be formed, e.g. the second electrode 230*b* may include a doped portion of the semiconductor body region 111.

Figure 10A:
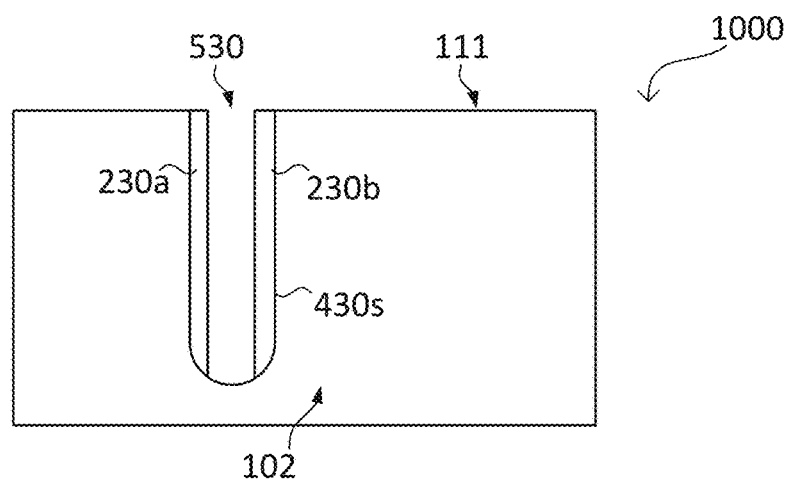
FIG. 10A to FIG. 10C respectively show a semiconductor chip at various stages during processing according to various embodiments.
Figure 10B:
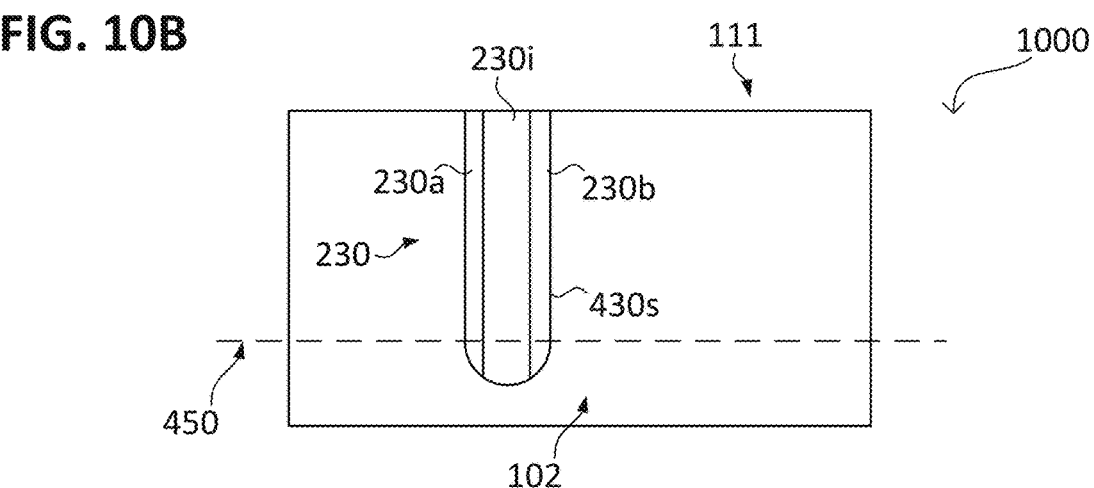

FIG. 10A and FIG. 10B respectively illustrate a semiconductor chip 1000 in a cross sectional view, during processing the semiconductor chip 1000, e.g. during a method for forming a capacitive structure 230 according to various embodiments.

A trench with a sidewall 430*s* may be formed in a semiconductor body 102 (not shown, see FIG. 4A). According to various embodiments, a first electrode 230*a* and a second electrode 230*b* may be formed in the trench, as illustrated in FIG. 10A. The first electrode 230*a* and the second electrode 230*b* may at least partially cover opposite sides of the sidewall 430*s* of the trench. The first electrode 230*a* and the second electrode 230*b* may be disposed at distance from each other. Further, the first electrode 230*a* and the second electrode 230*b* may form a recess 530 and may be disposed at opposite sides of the recess 530.

According to various embodiments, an electrically insulating region 230*i* may be formed in the recess 530, as illustrated in FIG. 10B. The electrically insulating region 230*i* may at least partially fill the recess 530.

Figure 10C:
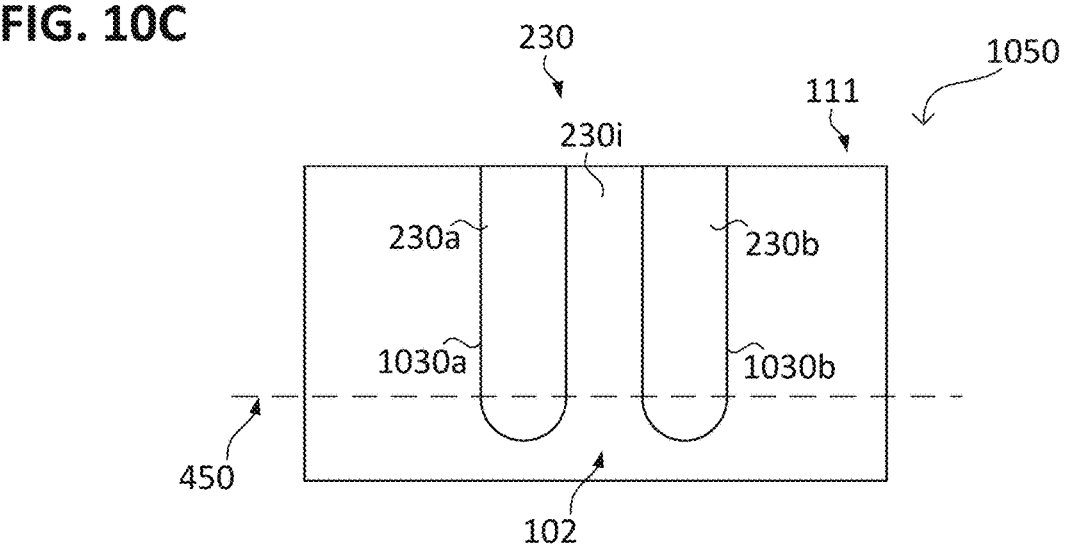

FIG. 10C illustrates a semiconductor chip 1050, according to various embodiments, in a cross sectional view (analog to FIG. 1A). The semiconductor chip 1050 may include a plurality of trenches including a first trench 1030*a* and a second trench 1030*b*. The first trench 1030*a* may include a first electrode region 230*a* of the capacitive structure 230; and the second trench 1030*b* may include a second electrode region 230*b* of the capacitive structure 230.

According to various embodiments, the first trench 1030*a* may be at least partially filled with a first metal or a first metal alloy and the second trench 1030*b* may be at least partially filled with a second metal or second metal alloy. The first metal or first metal alloy and the second metal or second metal alloy may be the same metal or metal alloy.

Figure 11A:
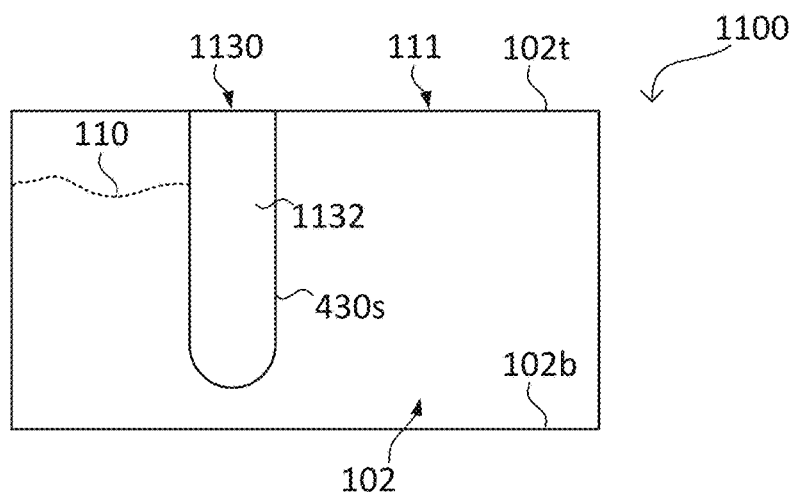
FIG. 11A to FIG. 11C respectively show a semiconductor chip at various stages during processing according to various embodiments.

FIG. 11A illustrates a semiconductor chip 1100, according to various embodiments, in a cross sectional view (analog to FIG. 1A). The semiconductor chip 1100 may include a crack absorption region 1130. The semiconductor body region 111 of the semiconductor chip 1100 may include a first surface 102*t*, e.g. a top surface 102*t*, and a second surface 102*b*, e.g. a bottom surface 102*b*, opposite the first surface 102*t*.

According to various embodiments, the crack absorption region 1130 may at least partially surround the semiconductor body region 111. Further, the crack absorption region 1130 may extend from the first surface 102*t* in a direction towards the second surface 102*b*. The crack absorption region 1130 may be configured to absorb chip crack 110 propagation. In other words, the crack absorption region 1130 may be configured to resist fracture and/or to prevent a crack 110 from propagating through the crack absorption region 1130 and/or to prevent a crack 110 from continuing to propagate from the crack absorption region 1130 into the semiconductor body region 111.

Therefore, the crack absorption region 1130 may include a crack absorption material 1132, in other words, a crack stop material 1132. The crack absorption material 1132 may define a fracture strain, in other words, an elongation at fracture of the crack absorption region 1130, which may be higher than the fracture strain of the semiconductor body region 111. The fracture strain may be seen as the maximum strain, in other words, the maximum elongation, of the crack absorption material 1132 at which the crack absorption material 1132 withstands crack formation. The strain of an elongated body, e.g. a solid body, may be defined from the fraction of the relative elongation, dL, of the body to the length of the body, L, before elongation. In other words, stretching a solid body in some direction results in an increment of the length L of the solid body by dL in that direction. The fracture strain may be understood as the relative elongation at which cracks into the solid body emanate, in other words, until the elongation results in material failure.

According to various embodiments, the crack absorption material 1132 may include a fracture strain greater than about 5%, e.g. greater than about 10%, e.g. greater than about 50%, e.g. greater than about 100%, e.g. greater than about 200%. According to various embodiments, the fracture strain of the crack absorption material 1132 is greater than a fracture strain of the semiconductor body 102, e.g. more than twice the fracture strain of the semiconductor body 102, e.g. more than five times the fracture strain of the semiconductor body 102, e.g. more than ten times the fracture strain of the semiconductor body 102. The fracture strain of the semiconductor body 102 may be defined by the semiconductor material of the semiconductor body 102, e.g. by a fracture strain of silicon.

According to various embodiments, the crack absorption material 1132 may include material with a small brittleness, e.g. a ductile material or an elastic material. For example, the crack absorption material 1132 may include a composite material or an elastomer, a rubber, imide, a metal, e.g. Aluminum, a printable polymer, a polymer resist, or a photoresist.

According to various embodiments, the crack absorption material 1132 may include a material with a fracture toughness greater than the fracture toughness of the semiconductor body region 111, e.g. a metal or a metal alloy. The fracture toughness may be seen as the ability of a material containing a crack to resist fracture, e.g. to resist a mechanical load (e.g. mechanical stress) without causing the crack to grow, or without failure in its mechanical properties. The fracture toughness of a material may be determined from the stress near the tip of a crack in the material caused by a remote mechanical load or caused by residual stresses at which the crack in the material begins to grow. For example, the fracture toughness of the crack absorption material 1132 may be greater than about 10 MPa m$^{1/2}$, e.g. greater than about 20 MPa m$^{1/2}$.

According to various embodiments, the crack absorption region 1130 may at least substantially extend from the first surface 102$t$ to the second surface 102$b$. For example, the crack absorption region 1130 may extend through the semiconductor body region 111.

According to various embodiments, the crack absorption material 1132 may be disposed in a trench 430 (see FIG. 4A). The trench 430 may extend into the semiconductor body 102. The trench 430 may at least partially be filled with the crack absorption material 1132.

Figure 11B:
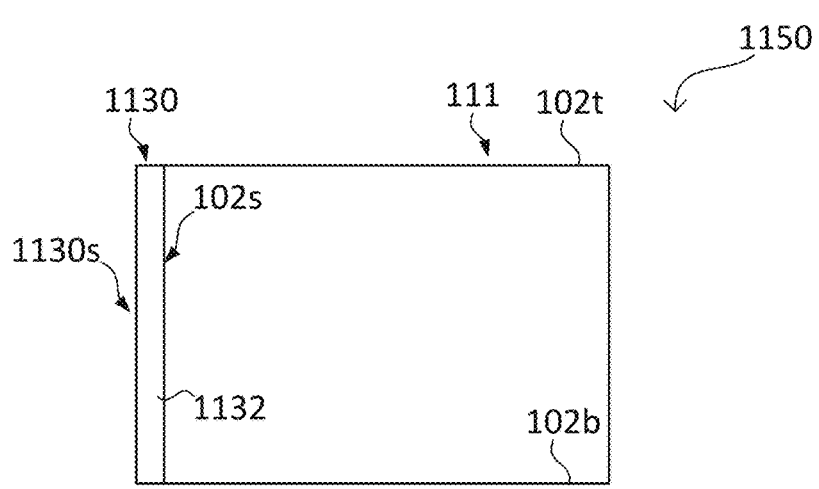

FIG. 11B illustrates a semiconductor chip 1150, according to various embodiments, in a cross sectional view (similar to FIG. 1A), wherein the crack absorption region 1130 may form a sidewall 1130$s$ of the semiconductor body region 111. According to various embodiments, the crack absorption material 1132 may be disposed on a sidewall 102$s$ of the semiconductor body region 111, e.g. after singulating the semiconductor chip 1150 from a wafer 702. According to various embodiments, the semiconductor chip 1150 may be singulated through the crack absorption material 1132, e.g. by cutting (e.g. by sawing) through the crack absorption material 1132.

Figure 11C:
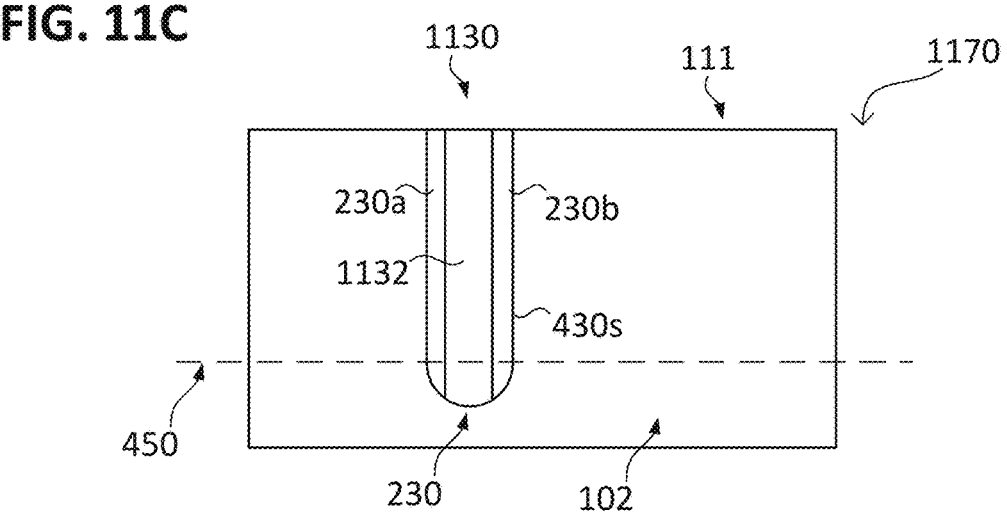

FIG. 11C illustrates a semiconductor chip 1170, according to various embodiments, in a cross sectional view (analog to FIG. 1A), wherein the semiconductor chip 1170 further includes a first electrode region 230$a$ and a second electrode region 230$b$ which may be configured, according to various embodiments, as described herein.

The first electrode region 230$a$ and the second electrode region 230$b$ may be disposed such that the crack absorption region 1130 extends between the first electrode region 230$a$ and the second electrode region 230$b$. For example, the crack absorption material 1132 may be disposed in a recess 530 which may be formed by the first electrode region 230$a$ and the second electrode region 230$b$ (see FIG. 10A).

According to various embodiments, the first electrode region 230$a$, the crack absorption region 1130 and the second electrode region 230$b$ may form a capacitive structure 230 for detecting crack propagation into the semiconductor body region, as described herein. The electrical properties of the crack absorption region 1130 may define a dielectric strength of the capacitive structure 230. According to various embodiments, the crack absorption region 1130 may include a dielectric crack absorption material 1132, e.g. a dielectric elastomer or a dielectric polymer.

According to various embodiments, the crack absorption material 1132 may include an insulating material, e.g. an insulating polymer, e.g. benzocyclobutene (BCB), an imide (e.g. polyimide (PI) or another imide), a resin, or a resist. The crack absorption material 1132 may be more deformable, e.g. more flexible, illustratively softer, compared to the semiconductor body 102, e.g. compared to silicon. The crack absorption material 1132 may provide absorbing "crack propagation" energy which enables crack propagation into the crack absorption material 1132. In other words, the crack absorption material 1132 may be suitable to absorb or stop crack propagation through the crack absorption material 1132. The crack absorption material 1132 may further provide an electrical isolation between the first electrode region 230$a$ and the second electrode region 230$b$, and may enable further to measure changes in the isolation, e.g. when a crack enters the crack absorption material 1132.

According to various embodiments, the crack absorption material 1132 may include a spin on glass material, e.g. a silicate or a siloxane or the like. For example, the crack absorption material 1132 (e.g. a spin on glass material or an imide) may be deposited or applied by rotation, e.g. by a spinning technique, e.g. in combination with a sol-gel technique. For example, the crack absorption material 1132 may be provided in a liquid form, e.g. as sol-gel or contained in a solvent, and introduced into the trench 430 by flow motion. After introducing the crack absorption material 1132 into the trench 430, the crack absorption material 1132 may be hardened, e.g. by tempering the crack absorption material 1132 or the whole semiconductor chip. Therefore, the crack absorption material 1132 may be secured in the trench 430 after being hardened. According to various embodiments, the crack absorption material 1132 may be porous after being hardened. A crack absorption material 1132 in porous form may be a moderate insulator, due to its inhomogeneities, however, porousness may increase the ability to stop or absorb a crack.

According to various embodiments, the crack absorption material 1132 may include a synthetic material, e.g. plastic, e.g. a polymer as described above. For example, the crack absorption material 1132 may be introduced into the trench 430 by injection molding.

FIG. 12 illustrates a schematic flow diagram of a method 1200 of processing a semiconductor chip (in other words, an integrated circuit, IC, chip, or microchip), wherein the method 1200 may include: in 1202 forming a trench in the semiconductor chip, the trench at least partially surrounding a semiconductor body region of the semiconductor chip and at least substantially extending from a first surface of the semiconductor body region to a second surface of the semiconductor body region opposite the first surface; and in 1204 forming a capacitive structure including a first electrode region, a second electrode region and an electrically insulating region extending between the first electrode region and the second electrode region; wherein at least the first electrode region is formed at least one of in or at the trench such that the first electrode region at least partially surrounds the semiconductor body region and at least substantially extends from the first surface to the second surface.

According to various embodiments, the first electrode region may be formed in the trench, e.g. deposited, in the trench (e.g. similar to FIG. 6A). The first electrode region may be formed at the trench, e.g. from a sidewall of the trench (e.g. similar to FIG. 4B). The method 1200 may further be configured in accordance with one or more embodiments described herein.

Figure 13:
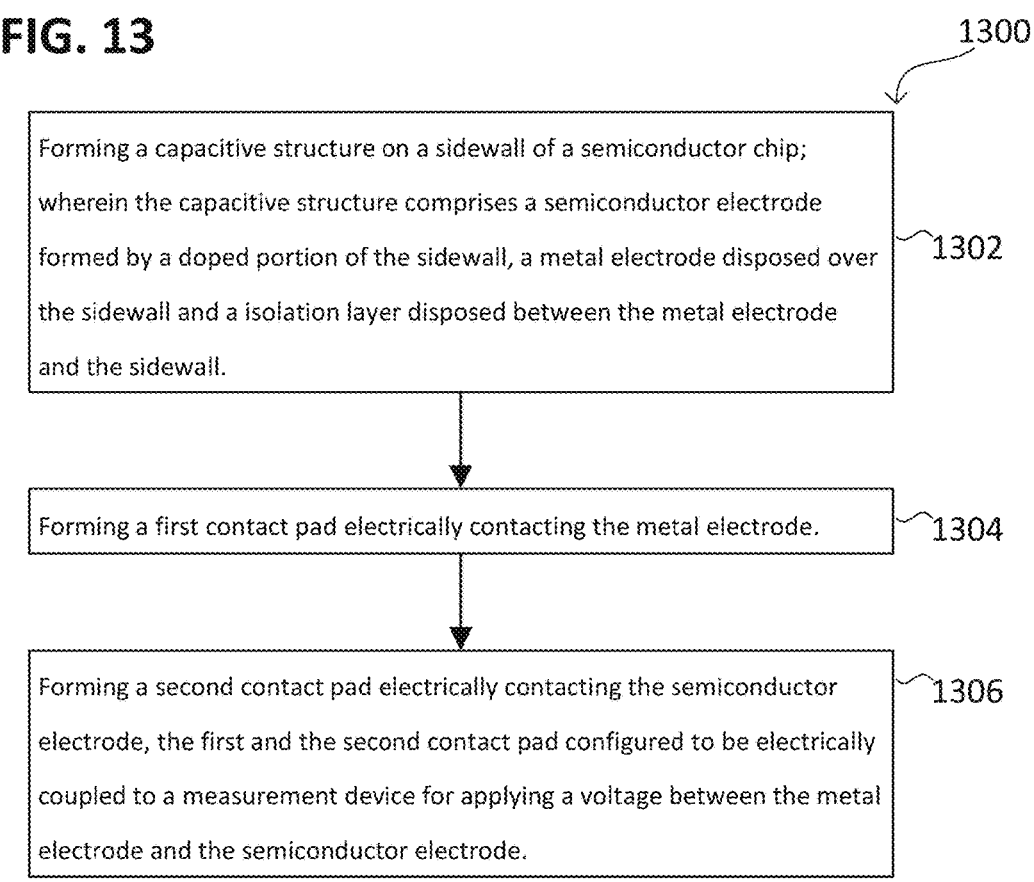
FIG. 13 shows a schematic flow diagram of a method of processing a semiconductor chip according to various embodiments.

FIG. 13 illustrates a schematic flow diagram of a method 1300 of processing a semiconductor chip, wherein the method 1300 may include: in 1302 forming a capacitive structure on a sidewall of the semiconductor chip; wherein the capacitive structure may include a semiconductor electrode (also referred as second electrode region including a semiconductor) formed by a doped portion of the sidewall, a metal electrode (also referred as first electrode region including a metal or metal alloy) disposed over the sidewall and an electrically insulating layer (also referred as electrically insulating region) disposed between the metal electrode and the sidewall; in 1304 forming a first contact pad electrically contacting the metal electrode; and in 1306 forming a second contact pad electrically contacting the semiconductor electrode, wherein the first and the second contact pad may be configured to be electrically coupled to a measurement device for applying a voltage between the metal electrode and the semiconductor electrode. The method 1300 may further be configured in accordance with one or more embodiments described herein.

FIG. 14 illustrates a schematic flow diagram of a method 1400 of processing a wafer (in other words, a carrier, e.g. a substrate), wherein the method 1400 may include: in 1402 forming a trench between a first semiconductor chip of the wafer and a second semiconductor chip of the wafer; wherein the trench may substantially extend from a first surface of the wafer to a second surface of the wafer opposite the first surface; in 1404 forming a capacitive structure in the trench; and in 1406 separating the first semiconductor chip from the second semiconductor chip, wherein the capacitive structure remains attached to the first semiconductor chip. The method 1400 may further be configured in accordance with one or more embodiments described herein.

FIG. 15 illustrates a schematic flow diagram of a method 1500 of processing a wafer, wherein the method 1500 may include: in 1502 forming a trench adjacent to a semiconductor chip of the wafer; the trench substantially extending from a first surface of the wafer to a second surface of the wafer opposite the first surface; in 1504 forming a capacitive structure in the trench, wherein the capacitive structure may include a first electrode region, a second electrode region disposed at a first side of the first electrode region, a third electrode region disposed at a second side of the first electrode region, a first electrically insulating region extending between the first electrode region and the second electrode region and a second electrically insulating region extending between the first electrode region and the third electrode region; wherein at least one of the first, the second and the third electrode regions substantially extends from the first surface of the wafer to the second surface of the wafer opposite the first surface; and in 1506 cutting the wafer through the trench, wherein at least the first electrode region and the second electrode region remain attached to the semiconductor chip. The method 1500 may further be configured in accordance with one or more embodiments described herein.

FIG. 16 illustrates a schematic flow diagram of a method 1600 of processing a wafer, wherein the method 1600 may include: in 1602 forming a trench adjacent to a semiconductor chip of the wafer; and in 1604 forming a crack absorption region in the trench, the crack absorption region extending from the first surface in a direction towards the second surface; wherein the crack absorption region may have a fracture strain greater than the semiconductor chip. The method 1600 may further be configured in accordance with one or more embodiments described herein.

FIG. 17 illustrates a schematic flow diagram of a method 1700 of processing a semiconductor chip, wherein the method 1700 may include: in 1702 forming a trench in the semiconductor chip; wherein the trench may at least partially surround a semiconductor body region of the semiconductor chip and may extend from a first surface of the semiconductor body region in a direction towards a second surface of the semiconductor body region opposite the first surface; and in 1704 forming a crack absorption region in the trench, wherein the crack absorption region may have a fracture strain greater than the semiconductor body region. The method 1700 may further be configured in accordance with one or more embodiments described herein.

According to various embodiments, a semiconductor chip may include: a semiconductor body region including a first surface and a second surface opposite the first surface; a capacitive structure for detecting crack propagation into the semiconductor body region; wherein the capacitive structure may include a first electrode region at least partially surrounding the semiconductor body region and at least substantially extending from the first surface to the second surface; wherein the capacitive structure further may include a second electrode region disposed next to the first electrode region and an electrically insulating region extending between the first electrode region and the second electrode region.

According to various embodiments, the second electrode region may at least partially surround the semiconductor body region.

According to various embodiments, the second electrode region may at least substantially extend from the first surface to the second surface.

According to various embodiments, the semiconductor chip may further include a first contact pad and a second contact pad, wherein the first electrode region may be electrically coupled to the first contact pad; and wherein the second electrode region may be electrically coupled to the second contact pad; wherein the first contact pad and the second contact pad may be configured to be electrically coupled to a measurement circuit for measuring a characteristic variable of the capacitive structure.

According to various embodiments, the semiconductor chip may further include the measurement circuit configured to measure a value of the characteristic variable of the capacitive structure by electrically characterizing the capacitive structure; wherein the measurement circuit may further be configured to determine a crack based on the measured value of the characteristic variable.

According to various embodiments, the first electrode region may include a first material and the second electrode region may include a second material.

According to various embodiments, the first material may be a first metal or first metal alloy and the second material may be a second metal or second metal alloy.

According to various embodiments, the first material and the second material may be the same material.

According to various embodiments, the first material may be a doped semiconductor of a first conductivity type (e.g. n-type doped) and the second material may be a doped semiconductor of a second conductivity type (e.g. p-type doped).

According to various embodiments, the first material may be a metal or metal alloy and the second material may be a doped semiconductor.

According to various embodiments, the electrically insulating region may include a dielectric material.

According to various embodiments, the capacitive structure may include a trench including the first electrode region, the second electrode region, and the electrically insulating region.

According to various embodiments, the first electrode region may include a first metal or first metal alloy at least partially filling the trench and the second electrode region may include a second metal or second metal alloy at least partially filling the trench.

According to various embodiments, the first electrode region may include a first semiconductor region of a first conductivity type including a sidewall of the trench, wherein the second electrode region may include a second semiconductor region of a second conductivity type; and wherein the electrically insulating region may include a depletion region formed by the first semiconductor region and the second semiconductor region.

According to various embodiments, the capacitive structure may include a first trench including the first electrode region, wherein the capacitive structure may include a second trench including the second electrode region.

According to various embodiments, the first electrode region may include a first metal or first metal alloy at least partially filling the first trench and the second electrode region may include a second metal or second metal alloy at least partially filling the second trench.

According to various embodiments, the semiconductor chip may further include a third electrode region disposed next to the first electrode region, and a further electrically insulating region extending between the third electrode region and the first electrode region.

According to various embodiments, the third electrode region and the second electrode region may be disposed at opposite sides of the first electrode region.

According to various embodiments, the first electrode region and second electrode region form a p-n-junction, wherein the electrically insulating region may include a depletion region of the p-n-junction.

According to various embodiments, a doped portion of the semiconductor body region may form the second electrode region.

According to various embodiments, an oxidized portion of the semiconductor body region, e.g. an oxide of the doped portion of the semiconductor body region, may form the electrically insulating region.

According to various embodiments, the first electrode region may form a sidewall of the semiconductor chip or a sidewall of the semiconductor body region.

According to various embodiments, the second electrode region may form a sidewall of the semiconductor chip or a sidewall of the semiconductor body region. The second electrode region may be disposed between the first electrode region and the semiconductor chip or semiconductor body region.

According to various embodiments, a semiconductor chip may include: a semiconductor body region including a first surface and a second surface opposite the first surface; a capacitive structure for detecting crack propagation into the semiconductor body region; wherein the capacitive structure may include a first semiconductor region of a first conductivity type, wherein the first semiconductor region may at least partially surround the semiconductor body region and may at least substantially extend from the first surface to the second surface; wherein the capacitive structure may further include a second semiconductor region of a second conductivity type, wherein the second semiconductor region may be disposed adjacent to the first semiconductor region.

According to various embodiments, the second semiconductor region may at least partially surround the semiconductor body region, wherein the second semiconductor region may at least substantially extend from the first surface to the second surface.

According to various embodiments, a semiconductor chip may include a semiconductor body region including a first surface and a second surface opposite the first surface; a capacitive structure for detecting crack propagation into the semiconductor body region; wherein the capacitive structure may include a first electrode region including a first metal or first metal alloy and a second electrode region including a second metal or second metal alloy disposed next to the first electrode region, wherein the first and second electrode region may at least partially surround the semiconductor body region and may at least substantially extend from the first surface to the second surface; and wherein the capacitive structure may further include an electrically insulating region disposed between the first electrode region and the second electrode region.

According to various embodiments, the capacitive structure may include a trench including the first electrode region, the second electrode region, and the electrically insulating region.

According to various embodiments, a semiconductor chip may include: a semiconductor body region including a top side, a bottom side opposite the top side and a lateral side extending between the top side and the bottom side; wherein the lateral side (e.g. a sidewall) may surround the semiconductor body region; a capacitive structure for detecting crack propagation into the semiconductor body region; wherein the capacitive structure may include a metal electrode over the lateral side and an electrically insulating layer disposed between the metal electrode and the lateral side; and wherein the capacitive structure may further include a semiconductor electrode formed by a doped portion of the semiconductor body region.

According to various embodiments, the electrically insulating layer may include an oxide of the doped portion of the semiconductor body region.

According to various embodiments, a semiconductor chip may include: a semiconductor body region including a first surface and a second surface opposite the first surface; a crack absorption region at least partially surrounding the semiconductor body region, wherein the crack absorption region may extend from the first surface in a direction towards the second surface; wherein the crack absorption region may include a fracture strain greater than the semiconductor body region.

According to various embodiments, the crack absorption region may substantially extend from the first surface to the second surface.

According to various embodiments, the crack absorption region may at least substantially extend from the first surface to the second surface.

According to various embodiments, the crack absorption region may include a ductile material.

According to various embodiments, the crack absorption region may include an elastomer.

According to various embodiments, the crack absorption region may include a polymer.

According to various embodiments, the crack absorption region may include a trench at least partially filled with at least one of a ductile material, an elastomer, and a polymer.

According to various embodiments, the crack absorption region may form a sidewall of the semiconductor chip.

According to various embodiments, the semiconductor chip may further include a first electrode region and a second electrode region, wherein the crack absorption region may extend between the first electrode region and the second electrode region, and wherein the first electrode region, the crack absorption region and the second electrode region may form a capacitive structure for detecting crack propagation into the semiconductor body region.

According to various embodiments, the crack absorption region may include a dielectric elastomer.

According to various embodiments, a method of processing a semiconductor chip may include forming a trench in the semiconductor chip, wherein the trench may at least partially surround a semiconductor body region of the semiconductor chip and may at least substantially extend from a first surface of the semiconductor body region to a second surface of the semiconductor body region opposite the first surface; forming a capacitive structure including a first electrode region, a second electrode region and an electrically insulating region extending between the first electrode region and the second electrode region; wherein at least the first electrode region may be formed at least one of in or at the trench such that the first electrode region may at least partially surround the semiconductor body region and may at least substantially extend from the first surface to the second surface.

According to various embodiments, the second electrode region may be formed in the trench such that the second electrode region may at least partially surround the semiconductor body region and may at least substantially extend from the first surface to the second surface.

According to various embodiments, the first electrode region may include a first metal or metal alloy, the second electrode region may include a second metal or metal alloy, and the electrically insulating region may include a dielectric material.

According to various embodiments, the method may further include: forming a further trench in the semiconductor chip, wherein the further trench may at least partially surround the semiconductor body region of the semiconductor chip and may at least substantially extend from the first surface of the semiconductor body region to the second surface of the semiconductor body region; wherein the second electrode region may be formed in the further trench such that the second electrode region may at least partially surround the semiconductor body region and may at least substantially extend from the first surface of the semiconductor body region to the second surface of the semiconductor body region; wherein the electrically insulating region may be formed from a portion of the semiconductor chip between the trench and the further trench.

According to various embodiments, the first electrode region may include a first metal or metal alloy, the second electrode region may include a second metal or metal alloy, and the electrically insulating region may include a dielectric material.

According to various embodiments, the second electrode region may be formed adjacent to the first electrode region and such that the second electrode region may at least partially surround the semiconductor body region; wherein the first electrode region may include a first semiconductor of a first conductivity type, the second electrode region may include a second semiconductor of a second conductivity type and the electrically insulating region may include a depletion region formed by the first and the second semiconductor.

According to various embodiments, forming the capacitive structure may include: depositing a dopant material into the trench; and outdiffusing a dopant from the dopant material into a sidewall of the trench, wherein the first electrode region may be formed from the outdiffused dopant.

According to various embodiments, outdiffusing the dopant from the dopant material may include heating the dopant material.

According to various embodiments, forming the capacitive structure may further include removing the dopant material from the trench after outdiffusing the dopant from the dopant material and at least partially filling the trench with a filling material. The filling material may include a conductive material.

According to various embodiments, forming the capacitive structure may include: depositing a further dopant material into the further trench; and outdiffusing a further dopant from the further dopant material into a sidewall of the further trench, wherein the second electrode region may be formed from the outdiffused further dopant.

According to various embodiments, forming the capacitive structure may further include removing the further dopant material from the further trench after outdiffusing the further dopant from the further dopant material and at least partially filling the further trench with a filling material.

According to various embodiments, forming the capacitive structure may further include: forming a third electrode region next to the first electrode region, wherein the third electrode region and the second electrode region may be disposed at opposite sides of the first electrode region; and forming a further electrically insulating region between the third electrode region and the first electrode region.

According to various embodiments, the third electrode region may include a third metal or metal alloy or a semiconductor of a third conductivity type. The third conductivity type may be the same as the second conductivity type. The third metal or metal alloy may be the same as the second metal or metal alloy.

According to various embodiments, the semiconductor chip may be part of a wafer and the method further may include separating the semiconductor chip from the wafer after forming the capacitive structure.

According to various embodiments, a method of processing a semiconductor chip may include forming a capacitive structure on a sidewall of the semiconductor chip; wherein the capacitive structure may include a semiconductor electrode formed by a doped portion of the sidewall, a metal electrode disposed over the sidewall and an electrically insulating layer disposed between the metal electrode and the sidewall; forming a first contact pad electrically contacting the metal electrode; and forming a second contact pad electrically contacting the semiconductor electrode, wherein the first and the second contact pad may be configured to be electrically coupled to a measurement device for applying a voltage between the metal electrode and the semiconductor electrode.

According to various embodiments, forming the electrically insulating layer may include oxidizing the sidewall of the semiconductor chip. The sidewall of the semiconductor chip may include a sidewall of the semiconductor body or a sidewall of the semiconductor body region.

The sidewall of the semiconductor chip may include a lateral side of the semiconductor chip, a lateral side of the semiconductor body or a lateral side of the semiconductor body region.

According to various embodiments, the semiconductor chip may be part of a wafer and the method further may include separating the semiconductor chip from the wafer after forming the capacitive structure.

According to various embodiments, a method of processing a wafer may include: forming a trench between a first semiconductor chip of the wafer and a second semiconductor chip of the wafer; wherein the trench may substantially extend from a first surface of the wafer to a second surface of the wafer opposite the first surface; forming a capacitive structure in the trench; and separating the first semiconductor chip from the second semiconductor chip, wherein the capacitive structure may remain attached to the first semiconductor chip.

According to various embodiments, a capacitive structure may include at least two electrode regions, e.g. a first electrode region and a second region. Further, a capacitive structure may include more than two electrode regions, e.g. three electrode regions, e.g. a first electrode region, a second region and a third region. Further, a capacitive structure may include four electrode regions, five electrode regions, or more than five electrode regions, e.g. ten electrode regions, e.g. twenty electrode regions.

According to various embodiments, the method may further include: forming a further capacitive structure in the trench, e.g. including at least two further electrodes; wherein the first semiconductor chip may be separated from the second semiconductor chip such that the further capacitive structure remains at the second semiconductor chip. The further capacitive structure may include the third electrode region and the further electrically insulating region (see e.g. FIG. 8B).

The first capacitive structure may at least substantially surround the first semiconductor chip, wherein the second capacitive structure may at least substantially surround the second semiconductor chip.

According to various embodiments, a method of processing a wafer may include forming a trench adjacent to a semiconductor chip of the wafer; wherein the trench may substantially extend from a first surface of the wafer to a second surface of the wafer opposite the first surface; forming a capacitive structure in the trench, the capacitive structure may include a first electrode region, a second electrode region disposed at a first side of the first electrode region, a third electrode region disposed at a second side of the first electrode region, a first electrically insulating region extending between the first electrode region and the second electrode region and a second electrically insulating region extending between the first electrode region and the third electrode region; wherein at least one of the first, the second and the third electrode region may substantially extends from the first surface of the wafer to the second surface of the wafer opposite the first surface; and cutting the wafer through the trench, wherein at least the first electrode region and the second electrode region may remain attached to the semiconductor chip.

According to various embodiments, the first surface of the wafer may include a first surface of the semiconductor chip or first surface of the semiconductor body region, e.g. if the semiconductor chip is part of the wafer. The second surface of the wafer may include a second surface of the semiconductor chip or second surface of the semiconductor body region, e.g. if the semiconductor chip is part of the wafer.

According to various embodiments, a method of processing a wafer may include forming a trench adjacent to a semiconductor chip of the wafer; forming a crack absorption region in the trench, wherein the crack absorption region may extend from the first surface in a direction towards the second surface; wherein the crack absorption region may include a fracture strain greater than the semiconductor chip. For example, the crack absorption region may include a fracture strain greater than the semiconductor body region.

According to various embodiments, a method of processing a semiconductor chip may include: forming a trench in the semiconductor chip; wherein the trench may at least partially surround a semiconductor body region of the semiconductor chip and may extend from a first surface of the semiconductor body region in a direction towards a second surface of the semiconductor body region opposite the first surface; forming a crack absorption region in the trench, wherein the crack absorption region may include a fracture strain greater than the semiconductor body region.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A semiconductor chip comprising:
    a semiconductor body region including a first surface and a second surface opposite the first surface; and
    a crack absorption region at least partially surrounding the semiconductor body region, wherein the crack absorption region extends from the first surface in a direction towards the second surface and wherein the crack absorption region includes a fracture strain greater than the semiconductor body region.

2. The semiconductor chip of claim 1, wherein the crack absorption region substantially extends from the first surface to the second surface.

3. The semiconductor chip of claim 1, wherein the crack absorption region extends at least from the first surface to the second surface.

4. The semiconductor chip of claim 1, wherein the crack absorption region comprises a ductile material.

5. The semiconductor chip of claim 1, wherein the crack absorption region comprises an elastomer.

6. The semiconductor chip of claim 1, wherein the crack absorption region comprises a polymer.

7. The semiconductor chip of claim 1, wherein the crack absorption region comprises a trench at least partially filled with at least one of a ductile material, an elastomer, and a polymer.

8. The semiconductor chip of claim 1, wherein the crack absorption region forms a sidewall of the semiconductor chip.

9. The semiconductor chip of claim 1, further comprising a first electrode region and a second electrode region, wherein the crack absorption region extends between the first electrode region and the second electrode region, and wherein the first electrode region, the crack absorption region and the second electrode region form a capacitive structure for detecting crack propagation into the semiconductor body region.

10. The semiconductor chip of claim 1, wherein the crack absorption region comprises a dielectric elastomer.

11. The semiconductor chip of claim 1, wherein the crack absorption region includes a fracture strain greater than about 5%.

12. The semiconductor chip of claim 1, wherein the crack absorption region includes a fracture strain greater than about 50%.

13. The semiconductor chip of claim 1, wherein the crack absorption region includes a fracture strain greater than about 100%.

14. The semiconductor chip of claim 1, wherein a fracture toughness of the crack absorption region is greater than about 10 MPa m1/2.

15. The semiconductor chip of claim 1, wherein the crack absorption region extends through the semiconductor body region.

16. A method for processing a wafer comprising:
- forming a trench adjacent to a semiconductor chip of the wafer; and
- forming a crack absorption region in the trench, wherein the crack absorption region extends from a first surface of the wafer in a direction towards a second surface of the wafer, the second surface being opposite to the first surface, wherein the crack absorption region includes a fracture strain greater than the semiconductor chip, wherein the crack absoprtion region forms a sidewall of a semiconductor body region of the semiconductor chip.

17. The method of claim 16, wherein the crack absorption region includes a fracture strain greater than the semiconductor body region of the semiconductor chip.

18. A method of processing a semiconductor chip comprising:
- forming a trench in the semiconductor chip, wherein the trench at least partially surrounds a semiconductor body region of the semiconductor chip and extends from a first surface of the semiconductor body region in a direction towards a second surface of the semiconductor body region opposite the first surface; and
- forming a crack absorption region in the trench, wherein the crack absorption region includes a fracture strain greater than the semiconductor body region.

* * * * *

UNITED STATES PATENT AND TRADEMARK OFFICE
CERTIFICATE OF CORRECTION

PATENT NO. : 10,522,432 B2
APPLICATION NO. : 15/413442
DATED : December 31, 2019
INVENTOR(S) : Herbert Gietler et al.

Page 1 of 2

It is certified that error appears in the above-identified patent and that said Letters Patent is hereby corrected as shown below:

On the Title Page

Below the abstract delete "18 Claims, 16 Drawing Sheets" and insert --18 Claims, 17 Drawing Sheets--

In the Drawings

Please insert the attached Drawing Sheet 3 of 17 between Drawing Sheets 2 and 3

Drawing Sheet 1; please change "Sheet 1 of 16" to --Sheet 1 of 17--
Drawing Sheet 2; please change "Sheet 2 of 16" to --Sheet 2 of 17--
Drawing Sheet 3; please change "Sheet 3 of 16" to --Sheet 4 of 17--
Drawing Sheet 4; please change "Sheet 4 of 16" to --Sheet 5 of 17--
Drawing Sheet 5; please change "Sheet 5 of 16" to --Sheet 6 of 17--
Drawing Sheet 6; please change "Sheet 6 of 16" to --Sheet 7 of 17--
Drawing Sheet 7; please change "Sheet 7 of 16" to --Sheet 8 of 17--
Drawing Sheet 8; please change "Sheet 8 of 16" to --Sheet 9 of 17--
Drawing Sheet 9; please change "Sheet 9 of 16" to --Sheet 10 of 17--
Drawing Sheet 10; please change "Sheet 10 of 16" to --Sheet 11 of 17--
Drawing Sheet 11; please change "Sheet 11 of 16" to --Sheet 12 of 17--
Drawing Sheet 12; please change "Sheet 12 of 16" to --Sheet 13 of 17--
Drawing Sheet 13; please change "Sheet 13 of 16" to --Sheet 14 of 17--
Drawing Sheet 14; please change "Sheet 14 of 16" to --Sheet 15 of 17--
Drawing Sheet 15; please change "Sheet 15 of 16" to --Sheet 16 of 17--
Drawing Sheet 16; please change "Sheet 16 of 16" to --Sheet 17 of 17--

Signed and Sealed this
Eighteenth Day of August, 2020

FIG. 3A
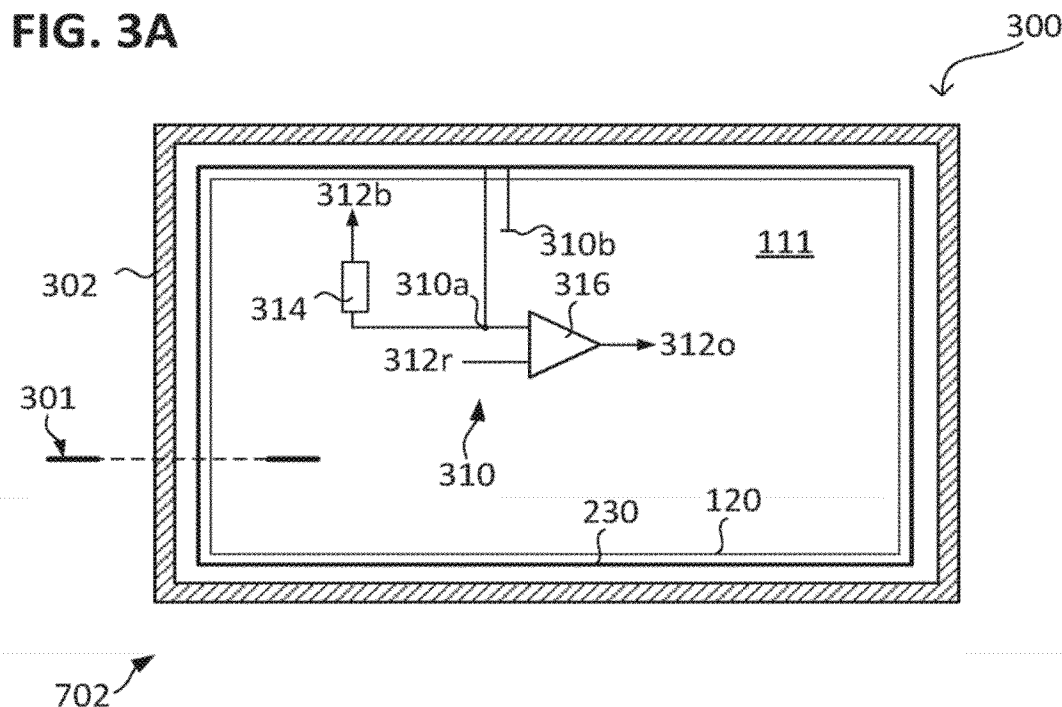
FIG. 3B
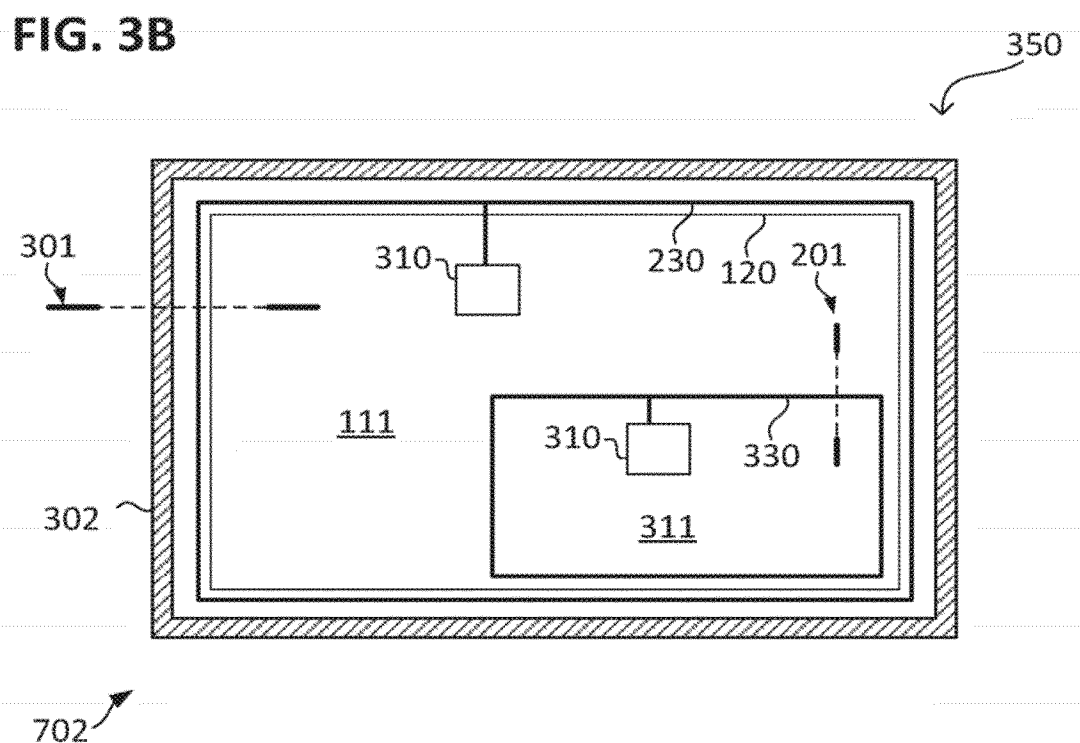

Andrei Iancu
*Director of the United States Patent and Trademark Office*